(12) United States Patent
Gorath

(10) Patent No.: US 9,248,099 B2
(45) Date of Patent: Feb. 2, 2016

(54) USE OF STABILIZED GRANULES CONTAINING GLYCERYL TRINITRATE FOR ARTERIOGENESIS

(71) Applicant: G. Pohl-Boskamp GmbH & Co. KG, Hohenlockstedt (DE)

(72) Inventor: Michaela Gorath, Hamburg (DE)

(73) Assignee: DESMOID AKTIENGESELLSCHAFT, Hamburg (DE)

( * ) Notice: Subject to any disclaimer, the term of this patent is extended or adjusted under 35 U.S.C. 154(b) by 78 days.

(21) Appl. No.: 13/904,325

(22) Filed: May 29, 2013

(65) Prior Publication Data

US 2014/0066502 A1 Mar. 6, 2014

Related U.S. Application Data

(60) Provisional application No. 61/653,601, filed on May 31, 2012.

(51) Int. Cl.
| | | |
|---|---|---|
| A61K 31/21 | (2006.01) | |
| A61K 9/14 | (2006.01) | |
| A61K 31/34 | (2006.01) | |
| A61K 31/616 | (2006.01) | |
| A61K 9/16 | (2006.01) | |
| A61K 9/00 | (2006.01) | |

(52) U.S. Cl.
CPC . *A61K 9/14* (2013.01); *A61K 9/006* (2013.01); *A61K 9/145* (2013.01); *A61K 9/1617* (2013.01); *A61K 9/1623* (2013.01); *A61K 31/21* (2013.01); *A61K 31/34* (2013.01); *A61K 31/616* (2013.01)

(58) Field of Classification Search
None
See application file for complete search history.

(56) References Cited

U.S. PATENT DOCUMENTS

| | | | |
|---|---|---|---|
| 3,155,574 | A | 11/1964 | Silson et al. |
| 4,323,577 | A | 4/1982 | Ohkuma et al. |
| 4,542,013 | A | 9/1985 | Keith |
| 4,919,919 | A | 4/1990 | Aouda et al. |
| 5,186,925 | A | 2/1993 | Cholcha |
| 5,370,862 | A | 12/1994 | Klokkers-Bethke et al. |
| 5,698,589 | A | 12/1997 | Allen |
| 5,744,124 | A | 4/1998 | Klokkers-Bethke et al. |
| 8,147,872 | B2 | 4/2012 | Crew et al. |
| 2002/0032232 | A1 | 3/2002 | Bing |
| 2003/0026849 | A1 | 2/2003 | Thomas |
| 2003/0078517 | A1* | 4/2003 | Kensey .............. 600/573 |
| 2003/0095925 | A1 | 5/2003 | Dugger, III |
| 2004/0228883 | A1 | 11/2004 | Karl |
| 2005/0192210 | A1 | 9/2005 | Rothbard et al. |
| 2007/0053966 | A1 | 3/2007 | Ang et al. |
| 2007/0059346 | A1* | 3/2007 | Maibach .............. 424/443 |
| 2009/0221540 | A1* | 9/2009 | Bennink .............. 514/171 |
| 2010/0016446 | A1 | 1/2010 | Gonda et al. |

FOREIGN PATENT DOCUMENTS

| | | |
|---|---|---|
| CA | 2718345 A1 | 9/2009 |
| DE | 3246081 A1 | 6/1984 |
| DE | 4038203 A1 | 6/1992 |
| DE | 102008005484 A1 | 7/2009 |
| EP | 0448961 A2 | 10/1991 |
| EP | 0461505 A1 | 12/1991 |
| EP | 0471161 A1 | 2/1992 |
| EP | 1004294 A1 | 5/2000 |
| GB | 1205019 A | 9/1970 |
| WO | 82/00005 A1 | 1/1982 |
| WO | 88/05306 A1 | 7/1988 |
| WO | 96/27372 A1 | 9/1996 |
| WO | 97/38687 A1 | 10/1997 |
| WO | 99/17766 A1 | 4/1999 |
| WO | 99/38472 A2 | 8/1999 |
| WO | 01/43735 A1 | 6/2001 |
| WO | 01/68062 A2 | 9/2001 |
| WO | 03/066472 A1 | 8/2003 |
| WO | 2004064779 A2 | 8/2004 |
| WO | 2005/004989 A1 | 1/2005 |
| WO | 2007/123955 A2 | 11/2007 |
| WO | 2008105731 A1 | 9/2008 |
| WO | WO 2008105731 A1 * | 9/2008 |
| WO | 2009/092358 A1 | 7/2009 |
| WO | 11/02606 A1 | 1/2011 |

OTHER PUBLICATIONS

U.S. Appl. No. 13/904,229, filed May 2013, Lee.*
Molecularinfo.com reference [Retrieved on Dec. 1, 2010 from the Internet: <URL: http://www.molecularinfo.com/MTM/D/D3/D3-r/D3-4-60.html], 1 pg.
Nitrolingual Pumpspray product insert (nitroglycerin lingual spray), G. Pohl-Boskamp GmbH & Co. KG, Oct. 2008, 4 pgs.
Nitrolingual Pumpspray package labelling (nitroglycerin lingual spray), G. Pohl Boskamp GmbH & Co. KG, Nov. 2008, 1 pg.
Nitrolingual Pumpspray bottle labelling (nitroglycerin lingual spray), G. Pohl-Boskamp GmbH & Co. KG, May 2006, 2 pgs.
Scheife et al., Journal of Pharmaceutical Sciences, vol. 71, Issue 1, Abstract, 1982, 1 pg.
Schranz et al., (1981), "Hemorrhagic pulmonary edema and cardiac failure following isolated head injury. Treatment with dobutamine and nitroglycerin," Monatsschr Kinderheilkd, 129 (4): 248-250. Abstract.

(Continued)

*Primary Examiner* — Svetlana M Ivanova
(74) *Attorney, Agent, or Firm* — K&L Gates LLP

(57) ABSTRACT

The present invention inter alia relates to a method of treating or preventing an arterial insufficiency, wherein an NO donor is administered in an intermitting manner to a subject in an amount effective for the induction of arteriogenesis, and wherein the NO donor is a solid pharmaceutical preparation with the active substance glyceryl trinitrate for oromucosal or oral administration characterized in that it contains between 0.05 and 2 weight % glyceryl trinitrate (GTN), at least one diluent, one carrier material, and at least one substance that reduces the volatility of GTN, whereby this substance is a non-volatile ester stabilizer whose melting point is not higher than 60° C.

8 Claims, 30 Drawing Sheets

(56) References Cited

OTHER PUBLICATIONS

Kuroda et al., (1997), "Changes in cerebral blood flow accompanied with reduction of blood pressure treatment in patients with hypertensive intracerebral hemorrhages," Neurol Res., 19(2): 169-73. Abstract.
International Search Report for International Application No. PCT/EP2011/003890, Date of Mailing Nov. 11, 2011. 6 pages.
Written Opinion for International Application No. PCT/EP2011/003890, Date of Mailing Nov. 11, 2011. 9 pages.
Fernandes et al., (2004), "Involvement of guanylate cyclase and potassium channels on the delayed phase of mouse carrageenan-induced paw edema," European Journal of Pharmacology, Elsevier Science, NL, vol. 501, No. 1-3, pp. 209-214.
Bel Trame et al., (1998) "Nitrate therapy is an alternative to furosemidel morphine therapy in the management of acute cardiogenic pulmonary edema," Journal of Cardiac Failure, vol. 4, No. 4, pp. 271-279.
International Search Report for International Application No. PCT/EP2009/001772, Date of Mailing Jun. 16, 2009. 3 pages.
Written Opinion for International Application No. PCT/EP2009/001772, Date of Mailing Jun. 16, 2009. 4 pages.
International Search Report for International Application No. PCT/EP2012/000803, Date of Mailing Jun. 25, 2012. 4 pages.
Written Opinion for International Application No. PCT/EP2012/000803, Date of Mailing Jun. 25, 2012. 7 pages.
M. J. Pikal et al: "Vapor pressure of nitroglycerin in sublingual molded tablets: Implications for stability", Journal of Pharmaceutical Sciences, 1976, vol. 65, No. 9, pp. 1278-1284.
M. J. Pikal et al: "Polymer sorption of nitroglycerin and stability of molded nitroglycerin tablets in unit-dose packaging", Journal of Pharmaceutical Sciences, 1977, vol. 66, No. 9, pp. 1293-1297.
M. J. Pikal et al: "Effect of nitroglycerin-soluble additives on the stability of molded nitroglycerin tablets", Journal of Pharmaceutical Sciences, 1984, vol. 73, No. 11, pp. 1608-1612.
"Glyceryl Monostearate", In: R C Rowe. P J Sheskey. S C Owen: "Handbook of Pharmaceutical Excipients, 5th Edition", 2005, Pharmaceutical Press, London.
International Search Report for International Application No. PCT/EP2012/000802, Date of Mailing Jun. 6, 2012. 4 pages.
Written Opinion for International Application No. PCT/EP2012/000802, Date of Mailing Jun. 6, 2012. 6 pages.
"Barex Resins", INEOS Barex, USA, 2006, Retrieved from the Internet: URL:http://www.ineosbarex.com/files/upload/Ineos%20Barex%20Brochure.pdf, retrieved on May 15, 2012, the whole document.
Daniel Banes: "Deterioration of nitroglycerin tablets", Journal of Pharmaceutical Sciences, vol. 57, No. 5, 1968, pp. 893-894.
European Search Report for EP12004187, Date of completion of search Sep. 28, 2012.
Cui X, et al., "Role of endothelial nitric oxide synthetase in arteriogenesis after stroke in mice", Neuroscience, New York, NY, US, vol. 159, No. 2, 2009, pp. 744-750.
Dinesh Kumar, et al., "Chronic sodium nitrite therapy augments ischemia-induced angiogenesis and arteriogenesis", Proceedings of the National Academy of Sciences, National Academy of Sciences, US, vol. 105, No. 21, 2008, pp. 7540-7545.
Hopkins et al., "Controlled delivery of vascular endothelial growth factor promotes neovascularization and maintains limb function in a rabbit model of ischemia", Journal of Vascular Surgery, C.V. Mosby Co., ST Louis, MO, US, vol. 27, No. 5, 1998, pp. 886-895.
Persson et al., "Therapeutic arterigenesis in peripheral arterial disease: Combining Intervention and Passive Training", Vasa Journal for Vascular Diseases, vol. 40, No. 3, 2011, pp. 177-187.
Sager H.B. et al., "Temporal patterns of blood flow and nitric oxide synthase expression affect macrophage accumulation and proliferation during collateral growth", J Angiogenes Res, 2010, vol. 2, No. 18, pp. 1-11.
Troidl K., et al., "Effects of Endogenous Nitric Oxide and of DETA NONOate in Arteriogenesis", J Cardiovsc Pharmacol, 2010, vol. 55, No. 2, pp. 153-160.
Troidl K. and Schaper W, "Arteriogenesis versus angiogenesis in peripheral artery disease", Diabetes/Metabolism Research and Reviews, 2012, vol. 28, S1, pp. 27-29.

* cited by examiner

10 DAYS RIP PBS:

10 DAYS SHAM PBS:

5 DAYS RIP PBS:

5 DAYS SHAM PBS:

5 DAYS SHAM NTG-PLACEBO:

5 DAYS SHAM NTG:

5 DAYS RIP NTG-PLACEBO:

5 DAYS RIP NTG:

5 DAYS RIP ISDN-PLACEBO:

5 DAYS RIP ISDN:

5 DAYS RIP ASA + PBS:

5 DAYS RIP ASA + NTG-PLACEBO:

5 DAYS RIP ASA + NTG:

USE OF STABILIZED GRANULES CONTAINING GLYCERYL TRINITRATE FOR ARTERIOGENESIS

CROSS-REFERENCE TO RELATED APPLICATIONS

This application claims the benefit under 35 U.S.C. §119(e) to U.S. Provisional Application No. 61/653,601, filed May 31, 2012, the entire disclosure of which is hereby incorporated herein by reference for all purposes.

FIELD OF INVENTION

The present invention relates to methods of treating or preventing an arterial insufficiency by the administration of a NO (nitric oxide) donor.

BACKGROUND

Cardiovascular diseases as well as other diseases involving a cardiovascular and, more specifically, arterial insufficiency have an enormous economic importance. In Germany, for example, about 280000 patients suffer every year from a cardiac infarct, while about 65000 patients die. One important reason for a cardiovascular disease is the partial or complete occlusion of arterial vessels resulting in a reduced supply of oxygen and nutrients of the tissue supplied by the arterial vessel.

Angina pectoris, the chest pain, is a clinical syndrome reflecting inadequate oxygen supply for myocardial metabolic demands with resultant ischemia and is generally caused by obstruction (stenosis) or spasm of coronary arteries.

Arteriogenesis is a process in which already pre-existing small arteriolar collaterals can develop to full functional conductance arteries which bypass the site of an arterial occlusion and/or compensate blood flow to ischemic territories supplied by the insufficient artery. Consequently, arteriogenesis is a highly effective endogenous mechanism for the maintenance and regeneration of the blood flow after an acute or chronic occlusive event in an arterial vessel. In this case the collaterals can function as natural bypasses.

Arteriogenesis is a process distinct from angiogenesis or neovascularization, where a de-novo formation of arterial vessels occur (Buschmann and Schaper, Journal of Pathology 2000, 190:338-342).

Nitroglycerin (glyceryl trinitrate) is used since decades as a vasodilatating agent in cardiovascular diseases as coronary artery disease (CAD, also ischemic heart disease or coronary artery disease), which is the leading cause of death and disability worldwide. Nitroglycerin has been solely used to treat the symptoms of these diseases e.g. stable angina pectoris due to its vasodilating effect on veins and arteries, resulting in a reduced workload and energy consumption of the heart (by decreasing preload and afterload) as well as an increased myocardial oxygen supply (by dilating the coronary arteries). These symptoms include chest pain, pressure, discomfort, or dyspnea. However, nitroglycerin has not been used for curing the underlying disease or improving its prognosis.

Consequently, nitroglycerin has been and is primarily used for the acute relief or prophylaxis of angina pectoris attacks, the most common symptom of CAD.

In the art, it has been described that nitroglycerin is not able to induce angiogenesis (neovascularisation) or arteriogenesis in a setting where this substance has been administered continuously (Hopkins et al. Journal of Vascular Surgery 27:886-894 (1998); Troidl et al. Journal of Cardiovascular Pharmacology 55: 153-160 (2010)).

There is a need for providing agents for promoting collateral circulation.

SUMMARY OF INVENTION

In a first aspect, the present invention relates to a method of treating or preventing an arterial insufficiency, wherein an NO donor is administered in an intermitting manner to a subject in an amount effective for the induction of arteriogenesis, and wherein the NO donor is glyceryl trinitrate in a solid pharmaceutical preparation for oromucosal or oral administration characterized in that it contains between 0.05 and 2 weight % glyceryl trinitrate (GTN), at least one diluent, one carrier material, and at least one substance that reduces the volatility of GTN, whereby this substance is a non-volatile ester stabilizer whose melting point is not higher than 60° C.

The invention further relates to a method of treating or preventing an arterial insufficiency, wherein an NO donor is administered in an intermitting manner to a subject in an amount effective for the induction of arteriogenesis, and wherein the NO donor is GTN in a solid pharmaceutical preparation for oromucosal or oral administration characterized in that it contains an absorbate comprising between 0.05 and 2 weight % GTN and a non-volatile ester stabilizer on a carrier material.

In the context of the present invention, it has been surprisingly found that NO donors are effective in the induction of arteriogenesis even if they are not administered constantly but in a manner where plasma levels are only elevated for a short time (see the example section). Consequently, the present invention provides effective agents for the promotion of collateral circulation. Based on the finding that NO donors are capable of inducing arteriogenesis, the present invention now provides an effective tool for preventing and treating an arterial insufficiency.

According to the present invention, the term "treatment" or "prevention" means that not only symptoms of the disease are relieved but that also the disease itself is treated or prevented. In a preferred embodiment, the term "treatment" means improving the prognosis of said disease.

According to the invention, the term "arterial insufficiency" refers to any insufficient blood or oxygen supply or any other insufficient supply of a tissue which is provided by an artery. This insufficient supply can be overcome by the methods and uses of the present invention wherein an NO donor is used to increase the supply of a given tissue. The arterial insufficiency may occur both during physical rest or during an exercise.

In a preferred embodiment of the present invention, the arterial insufficiency is due to insufficient oxygen or blood supply of a tissue supplied by the artery or a bypass or shunt during physical rest or exercise.

According to a further preferred embodiment, the arterial insufficiency is due to an increased demand of oxygen or blood flow of a tissue supplied by the artery or a bypass or shunt.

This increased demand of oxygen or blood flow can have several reasons including but not limited to increased sport or physical activity, and increased mental activity or a disease requiring an increased demand of oxygen or blood flow.

According to a further preferred embodiment, the arterial insufficiency is characterized by a partial (stenosis) or complete occlusion of an arterial vessel. In the context of the present invention, the term "partial occlusion" is equivalent to a stenosis.

The partial or complete occlusion of an arterial vessel is a well-known phenomenon. It can have various reasons including but not limited to deposition of material in the blood vessels (including non-revascularisable stenoses), compression from external tissue or fluid next to the vessel or a dysfunction of the endothelium of the vessel resulting in a paradoxic vasoconstriction during exercise.

In a preferred embodiment, the arterial insufficiency is due to the deposition of material in the blood vessels.

The deposition of materials in the blood vessels is a well-known phenomenon resulting e.g. in atherosclerosis.

In a further preferred embodiment, the arterial insufficiency is due to an external or internal compression of an artery.

An internal compression of an artery may be due to an edema but also to a tumor putting pressure on the artery. Furthermore, this includes a vasospastical constriction of the artery as e.g. in Prinzmetal's angina. In addition, this also includes the paradoxic vasoconstriction which e.g. sometimes occur in an endothelial dysfunction.

An external compression may be due to an accident or any external force which can put pressure on an artery.

In a further preferred embodiment, the arterial insufficiency is a vascular disease.

According to a further preferred embodiment, the arterial insufficiency is a disease selected from the group consisting of atherosclerosis, an ischemic disease and a further chronic arterial disease.

In a further preferred embodiment, the arterial insufficiency is a coronary arterial insufficiency.

In a preferred embodiment, the coronary insufficiency is an atherosclerotic coronary arterial insufficiency, in particular coronary artery disease (coronary heart disease or ischemic heart disease), stable angina pectoris, unstable angina pectoris, myocardial ischemia or chronic myocardial ischemia, acute coronary syndrome, or myocardial infarct (heart attack or ischemic myocardial infarct).

In a further preferred embodiment, the coronary insufficiency is a non-atherosclerotic, in particular coronary microvascular disease or small vessel disease, Prinzmetal's angina and cardiac syndrome X.

In a further preferred embodiment, the arterial insufficiency is a cerebral arterial insufficiency.

In a preferred embodiment, the cerebral arterial insufficiency is an atherosclerotic cerebral arterial insufficiency, in particular cerebral ischemia, pre-stroke, transient ischemic attack (mini stroke), stroke, vascular dementia, ischemic brain disease, or ischemic cerebrovascular disease.

The cerebral arterial insufficiency may also be ischemic microvascular brain disease, small vessel vascular dementia, subcortical arteriosclerotic encephalopathy (Binswanger's disease), Alzheimer's disease, or Parkinson's disease.

In a preferred embodiment, the arterial insufficiency is a peripheral arterial insufficiency.

In a preferred embodiment, the peripheral arterial insufficiency is an atherosclerotic peripheral arterial insufficiency, in particular peripheral vascular disease (peripheral artery disease (PAD) or peripheral artery occlusive disease (PAOD)).

In a preferred embodiment, the peripheral arterial insufficiency is an non-atherosclerotic peripheral arterial insufficiency, in particular Raynaud's syndrome (vasospasmatic), thrombangiitis obliterans, endangitis obliterans or Buerger's disease (recurring progressive inflammation and thrombosis (clotting) of small and medium arteries and veins of the hands and feet), vascular inflammatory disease (vasculitis), diabetic ischemia, diabetic neuropathy and compartment syndromes.

In a further preferred embodiment, the arterial insufficiency may be an intestinal arterial insufficiency, in particular an atherosclerotic intestinal arterial insufficiency, in particular ischemic bowel disease, mesenteric ischemia, or mesenteric infarction.

In a further preferred embodiment, the arterial insufficiency may be an urogenital arterial insufficiency, in particular an atherosclerotic urogenital arterial insufficiency, in particular erectile dysfunction, renal artery disease, renal ischemia, or renal infarction.

In a further preferred embodiment, the arterial insufficiency may be a nerval arterial insufficiency, in particular tinnitus.

Furthermore, the arterial insufficiency may be in the context of scleroderma (systemic sclerosis).

In a preferred embodiment, the arterial insufficiency is a central retinal artery insufficiency, in particular an atherosclerotic central retinal artery insufficiency, in particular ocular arterial insufficiency.

In a further preferred embodiment, the arterial insufficiency is characterized by an absence of an endothelial dysfunction.

The endothelial dysfunction is a well-known systemic pathological state of the endothelium and can be broadly defined as an imbalance between vasodilating and vasoconstricting substances produced by or acting on the endothelium.

In a further preferred embodiment, the arterial insufficiency is a chronic arterial insufficiency. In the context of the present invention, the term "chronic arterial insufficiency" means that the course of the arterial insufficiency is chronic and often progredient.

According to a further preferred embodiment, the chronic arterial insufficiency includes endothelial dysfunction, atherosclerosis, coronary artery disease (coronary heart disease or ischemic heart disease), stable angina pectoris, coronary microvascular disease or small vessel disease, Prinzmetal's angina and cardiac syndrome X, vascular dementia, ischemic brain disease, or ischemic cerebrovascular disease, ischemic microvascular brain disease, small vessel vascular dementia, subcortical atherosclerotic encephalopathy (Binswanger's disease), Alzheimer's disease, Parkinson's disease, peripheral vascular disease (peripheral artery disease (PAD) or peripheral artery occlusive disease (PAOD), thrombangiitis obliterans, endangitis obliterans or Buerger's disease, vascular inflammatory disease (vasculitis), diabetic ischemia, diabetic neuropathy, ischemic bowel disease, erectile dysfunction, renal artery disease, tinnitus, and scleroderma (systemic sclerosis).

The NO donor used in the context of the present invention is GTN which according to one aspect of the invention is in a solid pharmaceutical preparation for oromucosal or oral administration characterized in that it contains between 0.05 and 2 weight % glyceryl trinitrate (GTN), at least one diluent, one carrier material, and at least one substance that reduces the volatility of GTN, whereby this substance is a non-volatile ester stabilizer whose melting point is not higher than 60° C.

In the context of the present invention, the terms "GTN" or "nitroglycerin" are used simultaneously.

The present invention exploits the surprising finding that highly stable, non-liquid preparations of GTN can be manufactured using a novel process wherein GTN is combined with non-volatile carboxylic acid esters. Those esters which are suitable for this purpose are those with a melting point of 60° C. or less and which can be liquid or assume a pasty or semi-solid consistency at ambient temperatures ranging from about 15° C. to about 25° C. As described herein, it has now been discovered that a highly stabilized, non-liquid preparation of GTN results when GTN, phlegmatized in a suitable diluent to form a GTN concentrate, is then contacted with a suitable carrier material resulting in a GTN-containing slurry which is then (or contemporaneously) admixed with a suitable stabilizer in accordance with the teachings provided herein. The resulting GTN-containing absorbate is highly stable. The resulting absorbate can be in the form of a powder or granules. The absorbate can also be pressed to form a tablet type of composition. Without wishing to be bound by theory, the stabilizer entraps the GTN on and/or within the carrier material thereby preventing volatilization or escape of GTN from the non-liquid absorbate. Hence the invention results in highly prolonged shelf life and improved stability as compared with conventional GTN preparations, including GTN in a diluent customarily used for phlegmatization purposes.

The present invention is a significant advancement in the preparation and clinical availability of stabilized medicines with a prolonged shelf life whose active ingredient is, by its nature, volatile and unstable such as but not limited to GTN. The present invention has broad-reaching implications for medicinal chemistry and formularies heretofore unavailable.

Certain preferred preparations contain between 0.1 and 1 weight % glyceryl trinitrate. The non-volatile ester stabilizer can be solid or semi-solid at a temperature of 20° C. in certain preferred embodiments while the non-volatile ester stabilizer can be liquid in others. In preferred embodiments, the non-volatile ester stabilizer is selected from the group consisting of: mono- and diglycerides, polyethoxylated glycerides, esters of lactic acid, D-alpha tocopheryl polyethylene glycol 1000 succinate and solid triglycerides, and mixtures of any one of these substances. The non-volatile ester stabilizer can be used at a concentration of 0.2 to 10 weight %, based on the total weight of the preparation. According to the present invention, the GTN, diluent and stabilizer form a homogeneous preparation in some embodiments. In currently preferred embodiments, the mass ratio of the non-volatile ester stabilizer to GTN is between 2 and 40; and the mass ratio of the diluent to non-volatile ester stabilizer is between 1 and 9.5. In some preferred embodiments, the carrier material is selected from the group consisting of: magnesium aluminometasilicate, dibasic calcium phosphate, isomalt and mixtures of any one of the foregoing.

According to the present invention, the above-described solid pharmaceutical preparation can further include at least one excipient suitable for sublingual administration, which is selected from the group consisting of: water-soluble mono-, di-, and polysaccharides, as well as their alcohols. In currently preferred embodiments, the excipient suitable for sublingual administration is selected from the group consisting of: fructose, glucose, isomalt, lactose, maltose, maltitol, mannitol, sorbitol, sucrose, trehalose, and xylitol and mixtures of any one of the foregoing. In particularly preferred embodiments, the excipient suitable for sublingual administration is xylitol and/or isomalt at concentrations of between 20 and 95 weight %. In even more preferred embodiments, the excipient suitable for sublingual administration is isomalt, which is contained at concentrations of between 70 and 95 weight %, based on the total weight of the preparation.

In yet other embodiments of the solid pharmaceutical preparation, the preparation further comprises at least 0.01 to 3.0 weight % of a flavoring agent.

In one particularly preferred embodiment, the solid pharmaceutical preparation for oromucosal or oral administration contains an absorbate comprising between 0.05 and 2 weight % GTN and a non-volatile ester stabilizer on a carrier material.

According to the teachings of the present invention, any of the foregoing solid pharmaceutical preparation can be in the form of a free-flowing powder or free-flowing granules. They can be packaged as a single dose in the form of a stick pack or sachet.

In another aspect, the present invention provides a process for the manufacture of a pharmaceutical preparation with the active substance glyceryl trinitrate for oromucosal or oral administration characterized in that it contains between 0.05 and 2 weight % glyceryl trinitrate (GTN), the process comprising the steps of: a) preparing a mixture comprising at least one carrier material selected from the group consisting of: magnesium aluminometasilicate, dibasic calcium phosphate, fructose, glucose, isomalt, lactose, maltose, maltitol, mannitol, sorbitol, sucrose, trehalose, xylitol and mixtures of any one of the foregoing; b) preparing a GTN solution comprising at least one non-volatile ester stabilizer whose melting point is not higher than 60° C.; c) adding in a step-wise fashion the GTN solution to the carrier material; and d) mixing until the active substance has been homogeneously distributed, optionally followed by a drying step.

The preparation used in the context of the present invention may be produced by a process for the manufacture of a solid pharmaceutical preparation with the active substance GTN for oromucosal or oral administration characterized in that it contains between 0.05 and 2 weight % GTN, the process comprising the steps of: a) preparing a GTN solution comprising phlegmatized GTN and at least one non-volatile ester stabilizer; b) adding in a stepwise manner the GTN solution formed in step a) to a carrier material; c) optionally adding further excipients; d) mixing until the active substance has been homogeneously distributed, optionally followed by a drying step.

The preparation used in the context of the present invention may further be produced by a process for the manufacture of a solid pharmaceutical preparation with the active substance GTN for oromucosal or oral administration characterized in that it contains between 0.05 and 2 weight % GTN, the process comprising the steps of: a) providing GTN admixed with at least one non-volatile ester stabilizer; b) adding in a stepwise manner the GTN-stabilizer admixture of step a) to a carrier material; c) optionally adding further excipients; and d) mixing until the active substance has been homogeneously distributed, optionally followed by a drying step.

For purposes of clarification, and in no manner intended to be limiting, the following definition of terms used herein is provided:

Diluent is a substance which permits phlegmatization of a volatile substance such as GTN and permits safe preparation of a liquid concentrate. As also described elsewhere herein, suitable diluents include, for example (but not limited to), medium chain triglycerides (MCT) (e.g., $C_{6-12}$), propylene glycol and ethanol. For example, when reference herein is made to a GTN concentrate, it is GTN phlegmatized in a suitable diluent such as, for example, MCT.

Stabilizer is a substance which increases the stability of a volatile substance such as GTN beyond that exhibited by the substance in a mere diluent. As also described elsewhere herein, suitable stabilizers include but are not limited to non-volatile carboxylic acid esters. Generally speaking and as described elsewhere herein, suitable stabilizers can be selected from a group of carboxylic acid esters with similar polarity as GTN and which may be liquid, solid or semi-solid at ambient temperatures but liquefy at about 60° C. For purposes of the present invention, MCT such as, for example, medium chain triglycerides according to the European Pharmacopoeia are not contemplated as a stabilizer within the teachings of the present invention.

Carrier material is a non-liquid substance which renders a composition according to the present invention as a powder or a granule. As also described elsewhere herein, suitable carrier materials include but are not limited to water soluble carbohydrates and their respective alcohols such as, but not limited to, isomalt which has a porous structure and inorganic compounds with porous structures such as, but not limited to, anhydrous dibasic calcium phosphate and magnesium aluminometasilicate, or mixtures of any one of the foregoing.

Absorbate as used herein means a composition comprising an admixture of at least an active ingredient such as GTN in a phlegmatized form with at least one carrier material and a stabilizer. For purposes of the present invention, the mass ratio between diluent and stabilizer in one currently preferred embodiment is 19:5; in certain other preferred embodiments, the ratio is 19:10. In yet other preferred embodiments the diluent:stabilizer mass ratio is 19:2, 19:3, 19:4, 19:6, 19:7, 19:8, 19:9, 19:12, 19:15, and 1:1.

The teachings of the present invention have inter alia resulted in the surprising and unexpected finding that the free-flowing absorbate with its at least 10-fold greater surface area as compared with a conventional compressed tabletized form of GTN can minimize or prevent volatilization and/or evaporation of GTN, even though the GTN in theory has a greater opportunity to escape due to the absorbate's extensive surface area. One of skill in the art would not have predicted this based on the state of the art before the present invention.

Consequently, the present invention relates to the use of a GTN-containing pharmaceutical preparation which is stable during storage, in the form of a free-flowing powder or granules, which, in addition to at least one non-liquid carrier substance and optional additional excipients, comprises at least one stabilizer substance, which significantly reduces the volatility of GTN and is selected from the group of non-volatile esters whose melting point is not higher than 60° C. Without remaining bound by this theory, it is assumed that esters with a polarity very close to that of GTN surround the GTN molecules on the inner surface of the carrier material and prevent volatilization of the GTN. Stabilizers, which are solid, semi-solid or pasty at room temperature, are especially well suited as exemplified below. Again, without remaining bound by this theory, it is currently thought that the absorbed solutions which form the absorbate, which partially or completely solidify following preparation, are especially effective at trapping and thereby preventing the GTN from evaporating. For example, when a porous carrier is used, the GTN becomes encapsulated in the pores of the carrier as the stabilizer substance solidifies in the pores. The pharmaceutical preparation as described in the present invention is suitable for filling in individual packages, such as stick packs, capsules or sachets, for example. In the case of stick packs, particularly preferred materials and configurations are described in (1) International Patent Application PCT/EP2012/000802, the entire contents of which is herein incorporated by reference and (2) German Patent Application No. DE 10 2011 012 491.8 filed on Feb. 25, 2011. According to DE 10 2011 012 491.8 (e.g. example 5) the preferred materials for packaging the GTN containing preparation according to the invention are composite films which contain a layer comprising a copolymer of acrylonitrile units and one or more other monomers (AN-copolymers) on the surface facing the pharmaceutical preparation. In the case of stick packs, most preferred are aluminium composite films containing a layer made of acrylonitrile-methylacrylate copolymer or impact-modified acrylonitrile-methylacrylate copolymer on the side, which is in contact with the pharmaceutical composition. The pharmaceutical preparations and methods as described in the present invention can also be used, however, for the eventual production of other solid pharmaceutical forms, e.g. tablets, mini-tablets or pellets.

A particularly significant advantage of one aspect of the present invention is that production of pharmaceutical preparations of volatile, unstable ingredients can be carried out without the use of volatile and flammable solvents, enabling the preparations to be manufactured without the use of energy-intensive drying steps and elaborate solvent recovery processes. However, the present invention also contemplates production of pharmaceutical preparations of volatile ingredients such as GTN phlegmatized in ethanol.

Within the framework of the tests exemplified below, upon which the invention was discovered, it was unexpectedly discovered that the volatility of GTN is significantly reduced under both standard storage conditions as well as under stress conditions through the use of a non-volatile ester stabilizer whose melting point is not higher than about 60° C. For the purposes of the invention non-volatile means that the stabilizer substance preferably has a boiling point above or at about 200° C. (measured at normal ambient pressure). The preferred maximum melting point of 60° C. results from the fact that the GTN is also heated to this temperature during the absorbate production process. Higher temperatures should be avoided due to stability issues of the GTN. A more preferred melting point is at or about 0 to 50° C., an even more preferred melting point is at or about 20 to 45° C., and a most preferred melting point is at or about 30 to 40° C. Furthermore, and very importantly, the use of the ester stabilizer described herein does not compromise the disintegration properties of the granules, the release of the active substance, or its absorption into the body. The processes of the present invention result in a clinically advantageous composition, which induces a rapid absorption of the active substance when customarily administered via the oral mucosa and a resulting rapid reduction in the symptoms of the condition in life-threatening emergencies such as an attack of angina pectoris.

As described earlier, the present invention's GTN component is provided in the form of a phlegmatized GTN concentrate; in a preferred embodiment, the diluent for such a concentrate is MCT. Due to its explosive properties, GTN intended for pharmaceutical purposes is phlegmatized by the manufacturer, which reduces the risk posed by the hazardous properties. The matrix used for phlegmatization can be in liquid and/or powder form. For example, GTN is commercially available as a 5% solution in MCT, such as Miglyol® 812, as a 5% solution in propylene glycol, as a 10% concentrate in lactose triturate or a 2.25% dilution in glucose. Miglyol® 812 is a preparation comprising a fatty acid fraction of a maximum of about 2% caproic acid ($C_{6:0}$), about 50-80% caprylic acid ($C_{8:0}$), about 20-50% capric acid ($C_{10:0}$), a maximum of about 3% lauric acid ($C_{12:0}$), and a maximum of about 1% myristic acid ($C_{14:0}$) in keeping with the art-recognized standards set by the European Pharmacopoeia. If these GTN concentrates are used directly for the preparation of the absorbate according to the invention, then the diluent used for phlegmatization is also contained in the finished product. According to the present invention, a preferred ratio of diluent:stabilizer is between about 1 and 8; more preferably between about 1.2 and 5.0, even more preferably between about 1.5 and 4.0; and most preferably between about 1.9 and 3.8. In other equally useful embodiments of the present invention, GTN can be phlegmatized in a volatile solvent such as but not limited to ethanol; in such instances, little or no diluent is present in the finished product.

The stabilized GTN-containing composition according to the invention comprises an absorbate comprising concentrations of at or about 0.2 to 10 weight % of the non-volatile ester stabilizer having a melting point not higher than or at about 60° C.; stabilizer concentrations in certain preferred embodiments include 0.5, 1.0, 1.5, 2.0, 2.5, 3.0, 4.0, 5.0, 6.0, 7.0 or 8.0 weight %. It is also contemplated to use mixtures of the stabilizing esters described. In such cases, the quantities refer to the total for these substances. The GTN concentration in the final absorbate composition is within a range of at or about 0.05 to 2 weight %; in certain preferred embodiments GTN concentrations include 0.10, 0.15, 0.20, 0.25, 0.30, 0.35, 0.40, 0.50, 0.60, 0.70, 0.80, 1.0 or 1.5 weight %. Unless otherwise stated, all weight percentages refer to the total composition. The mass ratio of stabilizer(s):GTN is within the range of at or about 2 to 40; one preferred embodiment includes a ratio of 4 to 20, while a ratio of 5, 10, and 15 is particularly preferred in other embodiments.

As earlier explained, in a preferred embodiment of the invention the non-volatile ester stabilizer whose melting point is not higher than or at about 60° C. is selected from the group of liquid, solid, semi-solid or pasty substances at room temperature. In particularly preferred embodiments of the invention, the stabilizer is chosen from a group of substances that result in a homogeneous solution when admixed with the phlegmatized GTN concentrate. Especially preferred stabilizer substances are solid or pasty at room temperature, and include but are not limited to triglycerides, diglycerides, and monoglycerides; polyethoxylated triglycerides, diglycerides, and monoglycerides; esters of lactic acid; and D-alpha tocopheryl polyethylene glycol 1000 succinate (TPGS). As proposed earlier, it is suspected that the absorbates, which partially or completely solidify following preparation, are especially effective at preventing the GTN from evaporating.

In the case of stabilizers selected from the group consisting of triglycerides, preferred triglycerides include, for example, hard fat in accordance with USP/NF, which is, e.g., commercially available as Gelucire™ 43/01 from Gattefosse (Saint-Priest Cedex, France). In the case of mono- and diglycerides include, for example, glycerol monooleate, which is, e.g., commercially available as Cithrol® GMO HP from Croda GmbH (Nettetal, Germany), glycerol monocaprylocaprate in accordance with the European Pharmacopeia (Ph. Eur.), sold for example under the commercial name Capmul™ MCM EP by Abitec (Janesville, USA), or mono- and diglycerides in accordance with USP/NF. Polyethoxylated glycerides include for example oleoyl macrogol-6-glycerides in accordance with USP/NF, which are, e.g., commercially available as Labrafil® 1944CS from Gattefosse. In other embodiments, preferred stabilizers are selected from the group consisting of esters of lactic acid including, for example, cetyl lactate and myristyl lactate, which are, e.g., commercially available as Crodamol™ CL and Crodamol™ ML resp. from Croda GmbH (Nettetal, Germany).

The absorbate composition as used in the present invention also contains at least one pharmaceutically suitable carrier material characterized by a large inner surface area capable of absorbing, for example, oily liquids. Preferred carrier materials of that kind include, but are not limited to, magnesium aluminometasilicate in accordance with USP/NF, one example of which is commercially available as Neusilin® US2 from Fuji Chemical Industry (Japan), anhydrous dibasic calcium phosphate in accordance with USP/NF, one example of which is commercially available as Fujicalin® from Fuji Chemical Industry (Japan), isomalt according to the European Pharmacopoeia one example of which is commercially available as Galen IQ™ from BENEO-Palatinit GmbH (Mannheim, Germany) or mixtures of any one of the foregoing types of carrier materials.

The absorbate composition as used in the present invention can also contain other pharmaceutically acceptable excipients which support sublingual release of the active substance and are selected (but not limited to) from among the group water-soluble mono-, di-, and polysaccharides, as well as their alcohols. This excipient is selected especially from the group including but not limited to fructose, glucose, isomalt, lactose, maltose, maltitol, mannitol, sorbitol, sucrose, trehalose, and xylitol and/or mixtures thereof. In certain preferred embodiments, these excipients are present at a total concentration of at or about 70 to 95 weight %. In the case of mixtures the concentration of each individual substance is at or about 20 to 95 weight %, whereby in certain other preferred embodiments concentrations include 25, 30, 35, 40, 45, 50, 55, 60, 65, 70, 75, 80, or 85 weight %. In certain embodiments, isomalt is especially preferred. It can serve both as a carrier material when a diluent for the active ingredient such as GTN is an oily solution and can also serve as additional bulk material.

In addition, the absorbate preparation as used in the present invention can contain other excipients, such as flavoring agents. Flavoring agents are used especially in the case of preparations for oral or sublingual administration in order to increase acceptance among patients. In certain preferred embodiment according to the invention, they are used at concentrations of at or about 0.01 to 3.0 weight %, whereby the especially preferred concentrations in certain other embodiments include at or about 0.1, 0.5, 1, 1.5, 2 or 2.5 weight %.

A currently preferred formula comprises:

| Contents | Quantity [g] |
| --- | --- |
| GTN (5%) in diluent MCT | 79.35 |
| Glycerol monocaprylocaprate Ph. Eur. | 19.85 |
| Anhydrous dibasic calcium phosphate | 100.80 |
| Isomalt | 1800.00 |
| Total | 2000.00 |
| GTN concentration | 0.2% |

Another currently preferred formula comprises:

| Contents | Quantity [g] |
| --- | --- |
| GTN (5%) in diluent MCT | 40.0 |
| Solid Triglycerides | 20.0 |
| Anhydrous dibasic calcium phosphate | 49.9 |
| Isomalt | 880.1 |
| Peppermint flavoring agent | 10.0 |
| Total | 1000.00 |
| GTN concentration | 0.2% |

Yet another currently preferred formula comprises:

| Contents | Quantity [g] |
| --- | --- |
| GTN (5%) in diluent MCT | 40.0 |
| Oleoyl macrogol-6-glycerides | 20.0 |
| Anhydrous dibasic calcium phosphate | 50.0 |
| Isomalt | 880.0 |
| Peppermint flavoring agent | 10.0 |
| Total | 1000.00 |
| GTN concentration | 0.2% |

And, another currently preferred formula comprises:

| Contents | Quantity [g] |
| --- | --- |
| GTN (5%) in diluent MCT | 40.0 |
| Solid Triglycerides | 10.0 |
| Glycerol monocaprylocaprate Ph. Eur. | 10.0 |
| Anhydrous dibasic calcium phosphate | 50.0 |
| Isomalt | 880.0 |
| Peppermint flavoring agent | 10.0 |
| Total | 1000.00 |
| GTN concentration | 0.2% |

And, yet another currently preferred formula comprises:

| Contents | Quantity [g] |
| --- | --- |
| GTN (5%) in diluent MCT | 40.0 |
| Oleoyl macrogol-6-glycerides | 10.0 |
| Triglycerides | 10.0 |
| Anhydrous dibasic calcium phosphate | 50.0 |
| Isomalt | 880.0 |
| Peppermint flavoring agent | 10.0 |
| Total | 1000.0 |
| GTN concentration | 0.2% |

And, another currently preferred formula comprises:

| Contents | Quantity [g] |
| --- | --- |
| GTN (5%) in diluent propylene glycol | 4.0 |
| Glycerol monocaprylocaprate Ph. Eur. | 1.0 |
| Anhydrous dibasic calcium phosphate | 5.0 |
| Isomalt | 89.0 |
| Peppermint flavoring agent | 1.0 |
| Total | 100.00 |
| GTN concentration | 0.2% |

And, yet another currently preferred formula comprises:

| Contents | Quantity [g] |
| --- | --- |
| GTN (5%) in diluent propylene glycol | 4.0 |
| Oleoyl macrogol-6-glycerides | 2.0 |
| Anhydrous dibasic calcium phosphate | 5.0 |
| Isomalt | 88.0 |
| Peppermint flavoring agent | 1.0 |
| Total | 100.0 |
| GTN concentration | 0.2% |

And, another currently preferred formula comprises:

| Contents | Quantity [g] |
| --- | --- |
| GTN 5% in diluent ethanol | 4.0 |
| Glycerol monooleate | 4.0 |
| Anhydrous dibasic calcium phosphate | 5.0 |
| Isomalt | 89.8 |
| Peppermint flavoring agent | 1.0 |
| Total | 103.8 |
| GTN concentration after evaporation of ethanol | 0.2% |

And, yet another currently preferred formula comprises:

| Contents | Quantity [g] |
| --- | --- |
| GTN | 0.2 |
| Oleoyl macrogol-6-glycerides | 4.0 |
| Anhydrous dibasic calcium phosphate | 5.0 |
| Isomalt | 89.8 |
| Peppermint flavoring agent | 1.0 |
| Total | 100.0 |
| GTN concentration | 0.2% |

The method as described in the present invention comprises the mixture of a concentrate of a volatile chemical, such as for example a GTN concentrate in which GTN is solubilized in a suitable diluent with a non-volatile ester stabilizer whose melting point is not higher than about 60° C. until a homogeneous solution results. In certain embodiments, stabilizing esters not already in liquid form at room temperature are heated to a maximum temperature of about 10° C. above their melting point and then mixed with the GTN concentrate as described above at that temperature. This intermediate solution is then admixed with a carrier material which is powdered or granulated and mixed mechanically until a homogeneous, free-flowing powder or granulate absorbate is formed. For purposes of the present invention, free-flowing powder or granulate absorbate means an absorbate which does not have a wet or oily or sticky consistency or is not a liquid. In another embodiment, the GTN concentrate can first be combined with a carrier material capable of absorbing especially large quantities of oil—up to 100% of its own weight, for example—and then the other components such as the stabilizer can be added. Thus in certain embodiments in which the active substance now contained in a carrier material is mixed with the non-volatile ester stabilizer whose melting point is not higher than 60° C., it is possible to dispense entirely with the use of volatile and flammable solvents during the production process. This enables the production of a preferred embodiment of the absorbate according to the invention without energy-intensive drying steps and elaborate solvent recovery processes. Thus, one preferred embodiment of the production process of the present invention is especially suitable on an industrial scale. This is a significant advancement with industrial benefits heretofore unavailable.

However, as described earlier, other embodiments of the production process as described in the present invention contemplate the use of GTN concentrates comprising a volatile solvent such as ethanol. Even in the case of this particular production process, a heretofore unavailable stabilized free-flowing absorbate can still be successfully manufactured without any disadvantages or compromises in the resulting absorbate. In the case of an embodiment of the production method in which a GTN concentrate in a volatile diluent is used, the concentrate is absorbed by a solid carrier material and contemporaneously or in a second step the liquid or liquefied stabilizing ester is added. The resulting slurry is dried, for example at a temperature of 30° C. Then the other excipients are added and mixed until a homogeneous free flowing powder or granulate absorbate is formed.

In yet another embodiment of the production method as described in the present invention, GTN can be diluted under careful attention of the explosion risk directly in the stabilizing ester. This mixture is then absorbed by a solid carrier material. Then the other excipients are added and mixed until a homogeneous free flowing powder or granulate absorbate is formed. This process is most suitable when the stabilizer is a liquid.

In any of the proposed production methods described herein, a sieving or disaggregating step can be employed in order to ameliorate the flowing behavior of the powder mixture.

In yet another embodiment of the production method as described in the present invention, the method can differ from the above in that first a GTN concentrate is absorbed by a solid carrier material and second the liquid or liquefied stabilizing ester is added. Then the other excipients are added and mixed until a homogenous free flowing powder or granulate absorbate is formed. This process is especially effective if stabilizer and GTN in diluent cannot be mixed homogeneously e.g. solid triglycerides as stabilizers and GTN in diluent propylene glycol.

According to the invention, the NO donor is administered in an amount capable of inducing arteriogenesis. The skilled person will appreciate that this amount will depend on the subject to which the NO donor is administered. Generally, the amount to be administered may be between 0.1 and 8 mg per day, but this can vary due to the weight of the subject, its hemodynamic response to the NO donor and/or the severity of the disease.

In a preferred embodiment, the amount of the NO donor is applied in a dosage of 0.2 up to 0.8 mg (0.2, 0.3, 0.4, 0.6, 0.8) for at least 1-up to maximal 4-times daily, resulting in a maximal daily dosage of 3.2 mg.

According to the invention, the term "administration of an NO donor" means that a given dosage of the NO donor is administered. Depending on the way of administration, the skilled person will appreciate that the administration may take some time. In a preferred embodiment, the NO donor is administered in form of a chewable capsule, inhalable aerosol or powder, granules, powder or a tablet, which means that the administration may be completed within seconds. However, the administration of the NO donor may also take longer, e.g. if the NO donor is administered to the patient by way of infusion or by ointment or patch. Modes of administration of the NO donor are further discussed below.

Furthermore, according to the invention, the NO donor is administered in a manner capable of inducing arteriogenesis.

As shown in the examples, the inventors of the present invention have surprisingly found out that an NO donor is capable of inducing arteriogenesis when administered in an intermitting manner.

According to the invention, the term "intermitting manner" means that the NO donor is administered in a way that its plasma levels are only elevated in a short-term manner after the administration of the NO donor but then again decline. This can be achieved for example if the administration of GTN is followed by a time period without administration and then the NO donor is again administered to the subject. Furthermore, this way of administration avoids that the subject is developing tolerances against the effect of NO.

In a preferred embodiment, the plasma levels of the NO donor are elevated for not more that 180, 120, or 60 minutes, or for not more than 50, 40, 30, 15, 10 or 5 minutes.

Furthermore, this also implies that the NO donor can be administered in chronical manner, i.e. without taking account of disease developments implying an acute treatment with the NO donor. Furthermore, it also implies that a therapy plan can be established without taking account of disease developments implying an acute treatment with the NO donor.

In the context of the present invention, the NO donor is inter alia administered to induce arteriogenesis. This implies that the NO donor can also be administered at time points or time periods where there is no need for vasodilation and such a relief of symptoms like pain relief.

This is in contrast to past applications where an NO donor, e.g. nitroglycerin, has been used to achieve a relief or acute (i.e. immediate) prevention of the symptoms of a corresponding disease. These symptoms for example include pain and/or dyspnea in the case of a cardiovascular disease, and the relief or acute prevention of the symptoms was achieved by vasodilation and resulting pain and/or dyspnea relief. However, the purpose of the administration of the NO donor was, as discussed above, not the treatment of the underlying disease, because it was well known that the diseases cannot be treated by vasodilation or pain relief.

The identification of an NO donor as a pro-arteriogenic agent, therefore, also makes it possible that the NO donor is administered at time points or time periods where there is no need for such a relief of symptoms like pain relief. In a further preferred embodiment, the NO donor can also be administered in cases where there are no corresponding symptoms like dyspnea or pain or in cases where such symptoms are not to be expected.

In the context of the present invention, the term "intermittently" also means that the NO donor is not administered continuously. Rather, this term also means that there is an interval between two administrations of the NO donor, and that the NO donor is given several times, e.g. at least 1, 2, 3, 4, 5, 6, 8, 9, 12 or 16 times a day.

As the skilled person will appreciate, one administration of the NO donor may include an administration in one or more dosage forms, e.g. tablets. For example, one administration may include the administration of two tablets.

As to the schedule of administration, the skilled person will appreciate that there are many ways to achieve this intermitting administration. For example, it is possible to administer the NO donor at least once a day and at least on one day a week for at least two weeks. However, it is equally possible to administer the NO donor for only one week if the NO donor is administered several times during this week.

Preferable, the NO donor is administered once, twice or three times a day, wherein even more preferred the time period between two administrations of the NO donor is at least 4 hours, in particular 8 hours, in particular at least 10 hours or 12 hours.

Although possible, it is not necessary that the time periods between two administrations of the NO donor are the same. Rather, it is preferred that these time periods differ, depending on the individual administration schedule.

In a preferred embodiment, the NO donor is administered at least on one day a week. However, the NO donor may also be administered on 2, 3, 4, 5, 6 or 7 days a week. In an especially preferred embodiment, the NO donor is administered at least on 3 or 4 days a week.

According to the invention, it is possible to administer the NO donor for a period of several weeks or months. This is particularly preferred in order to induce arteriogenesis efficiently, although also a shorter administration of one of two weeks is possible.

In a preferred embodiment, the NO donor is administered for 2 to 8 weeks. It is equally preferred to administer the NO donor for 3 to 6, 3 to 8, 3 to 10 or 4 to 8, 4 to 10 or 4 to 12 weeks. These numbers are only examples and may vary depending on the individual schedule of the subject.

In a preferred embodiment, the NO donor is taken at least once a week for at least 8 weeks, in particular for at least 12 weeks.

In a further preferred embodiment, the NO donor is taken not longer than 6, 8 or 12 months. However, it is also possible to take the NO donor for 2, 3 or even more years. Furthermore, it is also possible that the NO donor is administered for decades or even through the whole life of the subject.

In the context of such long-term administrations, it is preferred that the NO donor is administered once or twice a week or at least once or twice a week.

It has been described previously that an exogenous stimulation of pulsatile shear forces in an individual may result in arteriogenesis. Furthermore, it has been described how the pulsatile shear forces can be measured (WO2010/072416).

Consequently, in a preferred embodiment, the NO donor is administered in conjunction with an exogenous stimulation of the pulsatile shear forces in the artery.

With respect to said embodiment of the invention, the NO donor should be administered in a way that it is active in the body of the subject when the exogenous stimulation is applied. In this context, active means that either the NO release is not yet terminated or the NO released from the NO donor is still present and active. Depending on the specific NO donor to be used, its physiological halftime in the subject and its formulation, the skilled person will be capable of determining when the NO donor has to be administered to the subject in order to ensure that it is active upon the exogenous stimulation.

In the case of nitroglycerin, the halftime and its persistence in the body of the subject has been intensively studied, e.g. after intravenous or sublingual application, where it is 2 to 5 minutes, see Armstrong et al. Circulation 59:585-588 (1979) or Armstrong et al. Circulation 62:160-166 (1980).

In a preferred embodiment, the NO donor is administered in the time period of 30, preferably 1 to 10 minutes before the onset of the exogenous stimulation until 30, preferably 1 to 10 minutes after the termination of the exogenous stimulation.

More preferably, the NO donor is administered in the time period of 15 minutes, preferably 5 minutes, more preferably 2 minutes before the exogenous stimulation until 30, preferably 15, more preferably 5 minutes after the onset of the exogenous stimulation.

In a further preferred embodiment, the NO donor is administered once a day, five times a week for 6 weeks 2-5 minutes before the exogenous stimulation.

The exogenous stimulation of the pulsatile shear forces may be achieved by any known way. This includes a stimulation with the help of medicaments like medicaments which increase the blood pressure.

In a preferred embodiment, said stimulation is achieved by physical exercise or the application of an endogenous force to the arterial vessel.

According to the invention, the term "physical exercise" means any training of the subject, including but not limited to training in exercise rooms, jogging, walking, nordic walking, swimming, dancing, cycling and hiking. The skilled person will appreciate that any exercise will be helpful in the context of the invention, provided that it is performed in conjunction with the administration of the NO donor. Preferably, the term "physical exercise" does not include unsupervised, unprescribed routine movements like casual walking or house work.

As discussed above, it has been found in the context of the present invention that an NO donor is capable of inducing arteriogenesis. This enables not only the treatment of an already existing disease. Rather, in the context of the present invention, it is also possible to prevent the disease. Consequently, in a preferred embodiment of the present invention, the method aims at the prevention of said arterial insufficiency.

As shown in the example section, in the context of the present invention, it has been possible to reduce the infarct size in case of an already existing occlusion. Furthermore, it has been possible to reduce arrhythmias in the subjects. Consequently, in a preferred embodiment of the present invention, the method results in a reduction of the infarct size, in reduced arrhythmias or in a decreased ST segment elevation.

The NO donor can be administered in any suitable way according to the invention so that it can be incorporated into the subject.

Consequently, in a preferred embodiment of the present invention, the NO donor is administered lingually, sublingually, bucally, or transmucosally.

In case of a lingual or sublingual administration, it is preferred that the NO donor, preferably nitroglycerin, is administered with the help of a chewable capsule or in the form of a tablet, powder or granules or even by an inhalator device, from which the NO donor can be easily inhaled and adsorbed. It is equally preferred that the NO donor is administered in the form of an aerosol or powder.

Preferably, the administration of the NO donor is a non-topical administration, i.e., that the NO donor is not administered to the skin of the subject. In the context of the present invention, the term "skin" excludes mucous membranes of the subject.

In a preferred embodiment, the NO donor is formulated in a way that allows a fast release of the NO donor from the formulation. This includes e.g. formulations which do not hold back the NO donor for a longer time period, but which release the NO donor within e.g. 10, 5 minutes or 1 minute or even in some seconds, e.g. 5 seconds.

Through the invention, it is preferred that the subject to which the NO donor is applied is a human subject.

In a further aspect, the present invention also relates to an NO donor as defined above for use in a method for the prevention or treatment of an arterial insufficiency, wherein the NO donor is administered in an amount and manner effective for the induction of arteriogenesis.

All features and preferred embodiments discussed above for the method of treating or preventing an arterial insufficiency also apply to the NO donor as defined above for use according to this aspect of the invention.

In another aspect, the present invention also relates to a method of the suppression of negative effects associated with any treatment of an arterial insufficiency which is anti-aterio-genic or inhibiting arteriogenesis, comprising administering to a subject subjected to said treatment an NO donor as defined above in an amount and manner effective for the induction of arteriogenesis.

In a preferred embodiment, said treatment is an acetyl salicylic acid (ASA), glycoproteinIIbIIIa antagonists, or etanercept (soluble tumor necrosis factor alpha receptor) treatment.

It is known in the art that ASA is an inhibitor of arteriogenesis (Singer et al., Vasa 2006, 35:174-177). Consequently, the ASA treatment of cardiovascular diseases, although being a standard therapy, has significant side effects and disadvantages. In the context of the present invention, it has been found that NO donors are capable of overcoming the genitive effects associated with an ASA treatment (see example section). Based on these findings, the inventors conclude that also the negative side effects associated with other medications like glycoproteinIIbIIIa antagonists or etanercept treatment can also be diminished.

Furthermore, the present invention also relates to an NO donor as defined above for use in a method of the suppression of negative effects associated with any treatment of an arterial insufficiency which is anti-ateriogenic or inhibiting arteriogenesis, wherein the NO donor is administered to a subject subjected to said treatment in an amount and manner effective for the induction of arteriogenesis.

In a preferred embodiment, said treatment is an acetyl salicylic acid (ASA), glycoproteinIIbIIIa antagonists, or etanercept (soluble tumor necrosis factor alpha receptor) treatment.

All features and preferred embodiments discussed above for the method of treating or preventing an arterial insufficiency also apply to the method for the suppression of negative effects according to this aspect of the invention or to said NO donor for use according to this aspect of the invention.

In a further aspect, the present invention also relates to a method for the prevention or treatment of a cardiac arrhythmia, wherein an NO donor as defined above is administered to a subject in an amount and manner effective for the treatment of said cardiac arrhythmia. Furthermore, the present invention also relates to an NO donor for use in a method for the prevention or treatment of a cardiac arrhythmia, wherein the NO donor is administered to a subject in an amount and manner effective for the treatment of said cardiac arrhythmia.

In the context of the present invention, the inventors have found that NO donors are capable to prevent and treat arrhythmias (see the example section).

All features and embodiments defined above with respect to the NO donor and its formulation and administration also apply to this method or NO or donor for use according to the invention.

The present invention also relates to a method of promoting collateral circulation comprising the step of exposing a subject to a therapeutically effective amount of an NO donor as defined above wherein the therapeutically effective amount of the NO donor promotes arteriogenesis sufficient to augment collateral circulation in a physiological or pathological condition.

The term collateral circulation describes the circulation of blood through so-called collateral vessels. These vessels are small arterioles, which are part of a network that interconnects perfusion territories of arterial branches. In the case that the main artery itself is not capable of sufficiently supplying a tissue, e.g. due to an arterial occlusion, these collateral vessels are recruited and can develop to large conductance arteries, to bypass the site of an arterial occlusion and/or to compensate blood flow to ischemic territories supplied by the or insufficient artery. In the context of the present invention, the promotion of collateral circulation occurs via arteriogenesis.

According to the invention, the term "physiological condition" denotes any condition of the subject which is not related to any disease.

According to the invention, the term "pathological condition" denotes any condition of the subject which is related to a disease.

Preferably, the subject suffers from an arterial insufficiency.

All features and preferred embodiments discussed above for the method of treating or preventing an arterial insufficiency also apply to the method of promoting collateral circulation.

With respect to the aspects defined above where the NO donor is administered in a manner sufficient to induce arteriogenesis this manner is preferably an intermitting manner as defined above.

The invention is further described by the attached figures and examples, which are intended to illustrate, but not to limit the invention.

ECG was recorded 90 minutes after FPO. Course of the ST elevation per beat at first 8 minutes revealed no differences between 5- and 10-days sham groups and 5-days RIP group. Only in the 10-days RIP group a lower ST elevation was observed.

Figure 2:
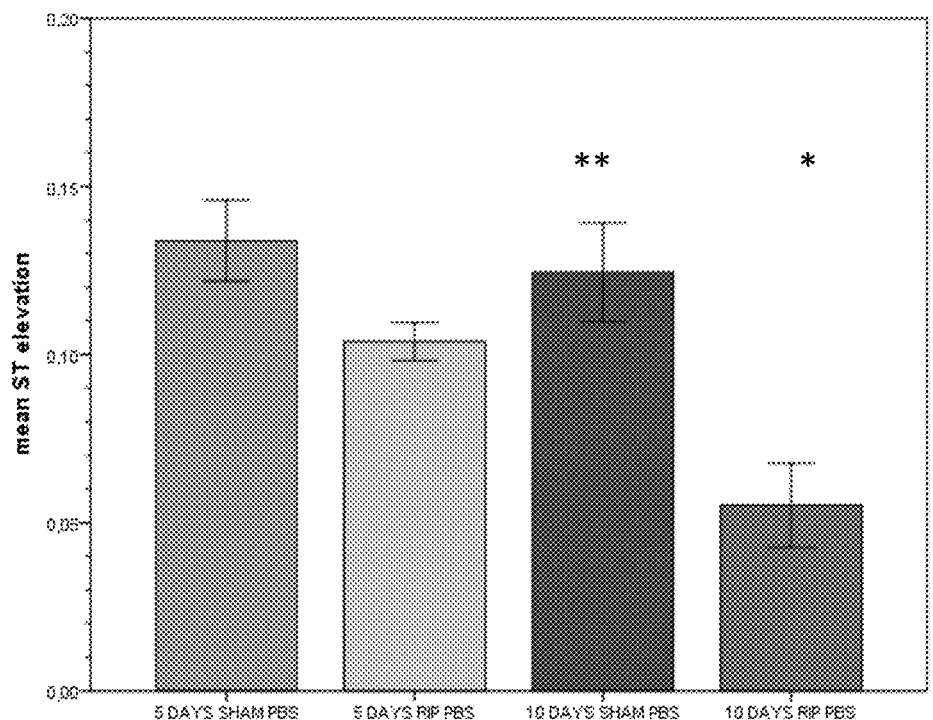

FIG. 2: ST segment elevation of 5- and 10-days-control-groups. Column 1 shows ST segment elevation of 5 DAYS SHAM PBS group; Column 2 shows ST segment elevation of 5 DAYS RIP PBS group; Column 3 shows ST segment elevation of 10 DAYS SHAM PBS group; Column 4 shows ST segment elevation of 10 DAYS RIP PBS group; standard deviation is indicated in error bars; one asterix indicates significant compared to 10 DAYS SHAM PBS (nominal p value <0.025); two asterix indicate significant compared to 10 DAYS RIP PBS (nominal p value <0.025).

Diagram shows mean of ST elevation maximum per group. After 5 days. There was no significant difference found between RIP and SHAM. After 10 days in the RIP group ST elevation maximum was significantly lower compared to sham (*) and 5-day RIP control (**) (*nominal p-value <0.025).

Figure 3:
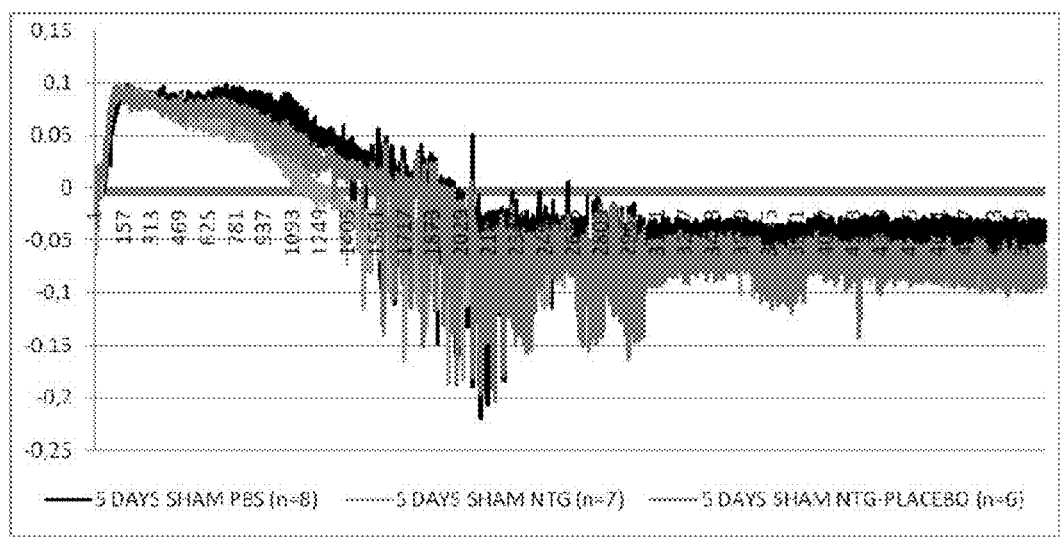

FIG. 3: Course of the ST elevation per beat after FPO (module 1: Sham operation without the RIP). ECG graph in black indicates 5 DAYS SHAM PBS, n=8: 0.134±0.034 mV, ECG graph in light grey indicates 5 DAYS SHAM NTG, n=7: 0.124±0.058 mV, ECG graph in middle grey indicates 5 DAYS SHAM NTG-PLACEBO, n=6: 0.131±0.043 mV.

The course of the ST elevation per beat after FPO revealed no differences between sham control and treated groups after 5 days.

Figure 4:
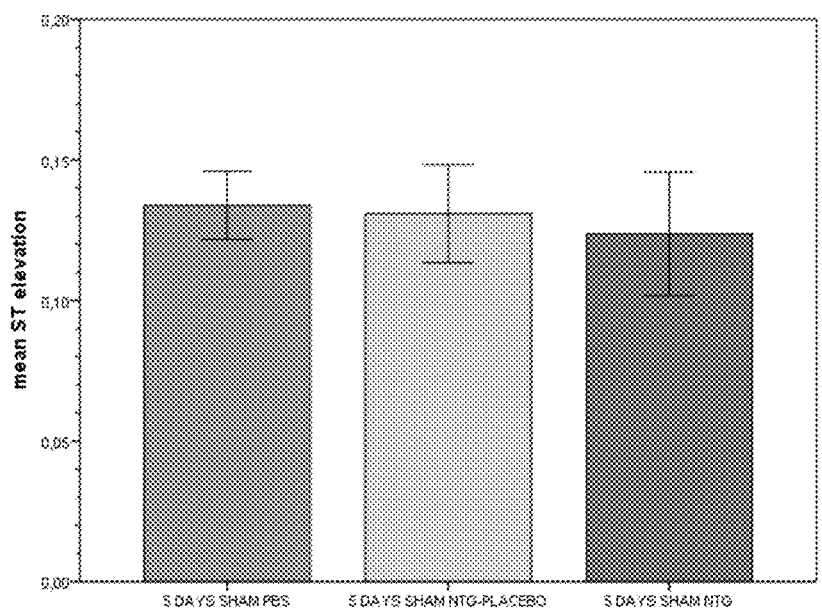

FIG. 4: ST segment elevation (module 1: Sham operation without the RIP). Column 1 shows 5 DAYS SHAM PBS; Column 2 shows 5 DAYS SHAM NTG-Placebo; Column 3 shows 5 DAYS SHAM NTG; standard deviation is indicated by error bars.

No difference in ST elevation maximum was found between sham control and treated groups.

Figure 5:
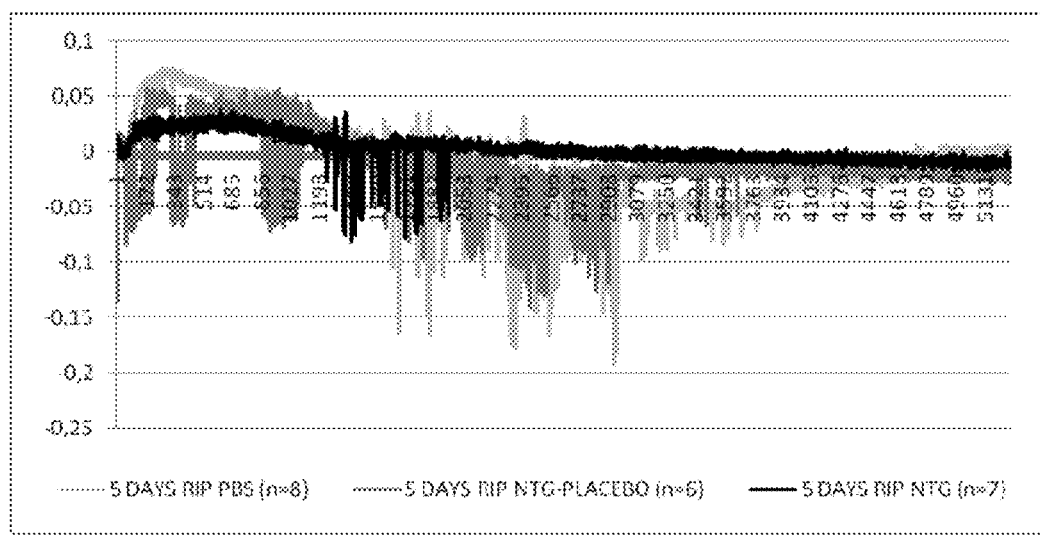

FIG. 5: Course of the ST elevation per beat after FPO (module 2: NO intermittend (NTG)). ECG graph in light grey indicates 5 DAYS RIP PBS, n=8: 0.104±0.016 mV; ECG graph in middle grey indicates 5 DAYS NTG-PLACEBO: n=6; 0.096±0.061 mV; ECG graph in black indicates 5 DAYS RIP NTG, n=7: 0.052±0.030 mV.

Compared to control treatment with PBS or NTG-Placebo a lower ST elevation course was detected after NTG treatment 5 days after RIP.

In the NTG group ("5 DAYS RIP NTG") ST elevation is significantly decreased compared to the PBS group. There is no significance between the PBS and NTG-PLACEBO-group.

Figure 6:
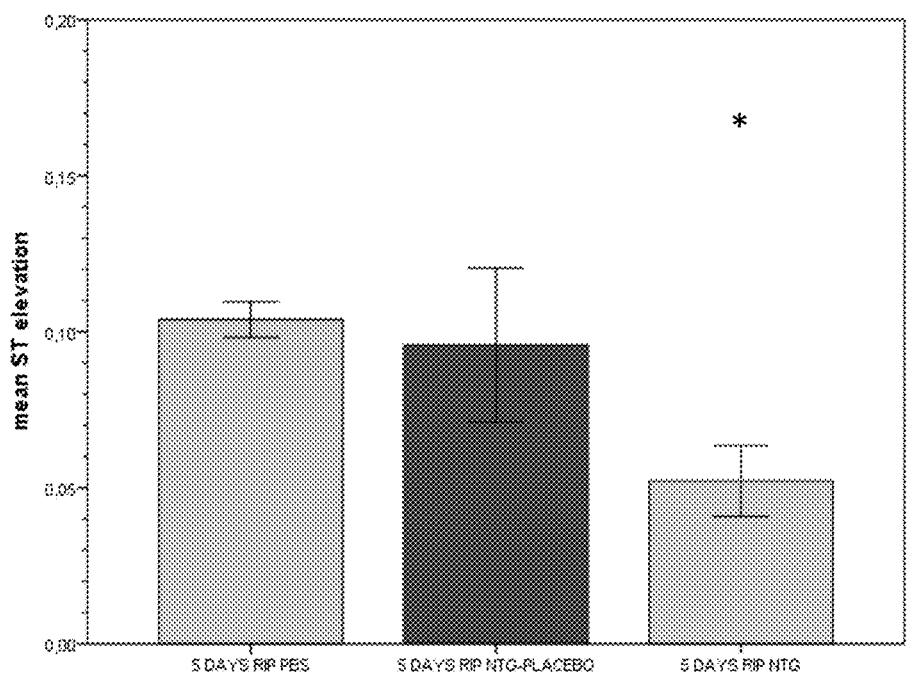

FIG. 6: ST segment elevation (module 2: NO intermittend (NTG)). Column 1 shows 5 DAYS RIP PBS; Column 2 shows 5 DAYS NTG-PLACEBO; Column 3 shows 5 DAYS RIP NTG; standard deviation is indicated by error bars, asterix indicates significant decrease of ST elevation compared to PBS group (nominal p-value <0.017).

After treatment with NTG, the ST elevation maximum was significantly decreased compared to PBS and NTG-Placebo treatment 5 days after RIP (*nominal p-value <0.017).

Figure 7:
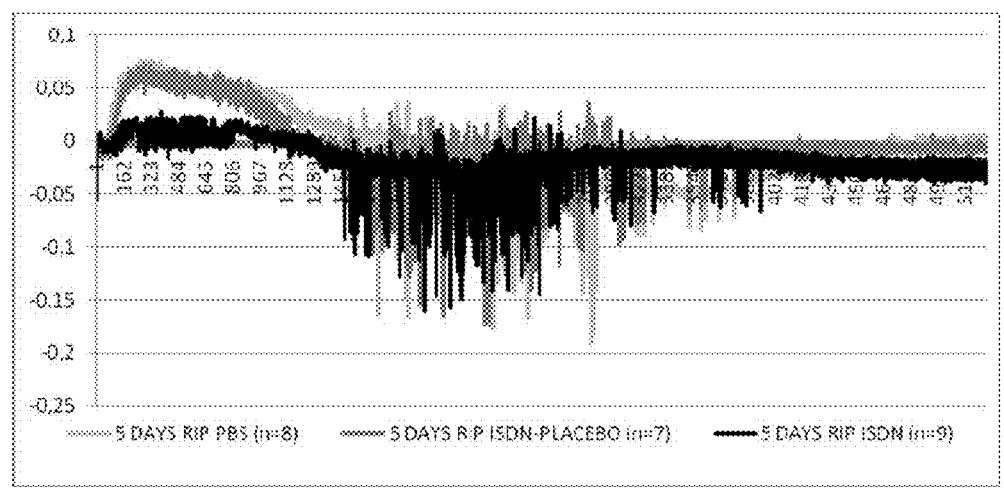

FIG. 7: Course of the ST elevation per beat after FPO (module 3: NO continuous (ISDN retard)). ECG graph in light grey indicates 5 DAYS RIP PBS, n=8: 0.104±0.016 mV; ECG graph in middle grey indicates 5 DAYS ISDN-PLACEBO, n=7: 0.110±0.069 mV; ECG graph in black indicates 5 DAYS RIP ISDN, n=7: 0.062±0.027 mV.

Compared to control treatment with PBS or ISDN-Placebo a lower ST elevation course was detected after ISDN treatment 5 days after RIP.

ST segment elevation in the ISDN group ("5 DAYS RIP ISDN") is decreased compared to the PBS group but there is no significance as well as between the PBS and ISDN-PLACEBO-group.

Figure 8:
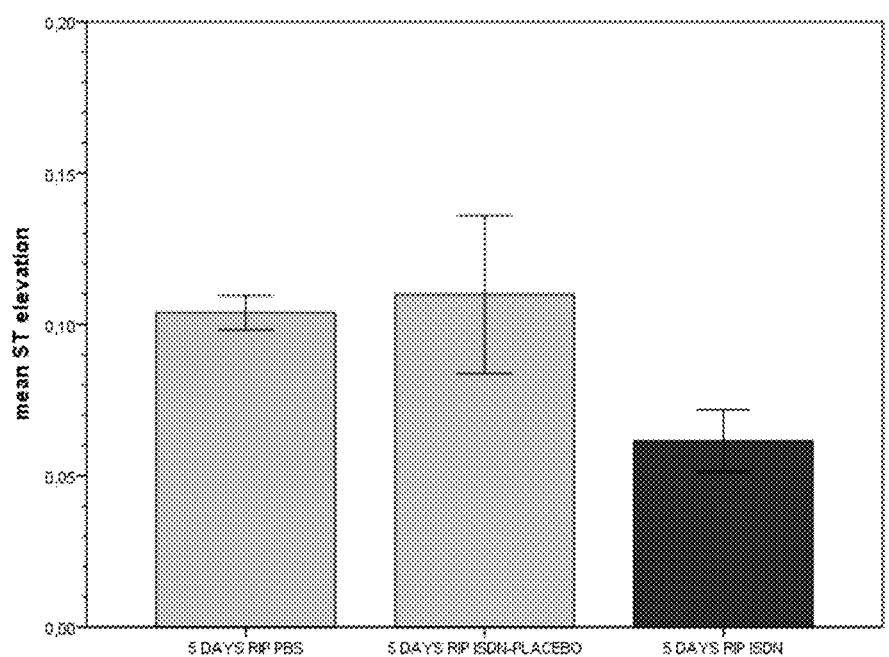

FIG. 8: ST segment elevation (module 3: NO continuous (ISDN retard)). Column 1 shows 5 DAYS RIP PBS; Column 2 shows 5 DAYS RIP ISDN-PLACEBO; Column 3 shows 5 DAYS RIP ISDN; standard deviation is indicated by error bars.

After treatment with ISDN, the ST elevation maximum was non-significantly decreased compared to PBS and ISDN-Placebo treatment 5 days after RIP (nominal p-value <0.017).

Figure 9:
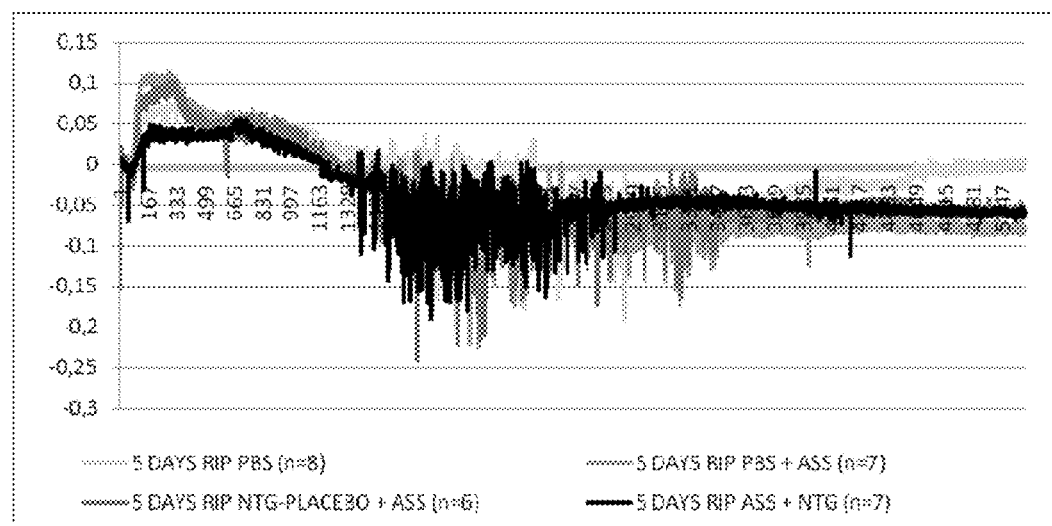

FIG. 9: Course of the ST elevation per beat after FPO (module 4: NO intermittent plus ASA). ECG graph in light grey indicates 5 DAYS RIP PBS, n=8; 0.104±0.016 mV; ECG graph in middle grey indicates 5 DAYS RIP ASA+PBS, n=7: 0.138±0.098 mV; ECG graph in dark grey indicates 5 DAYS RIP ASA+NTG-PLACEBO, n=6: 0.144±0.091 mV; ECG graph in black indicates 5 DAYS RIP NTG+ASA, n=7: 0.088±0.071 mV. Treatment with NTG+ASA was compared to with PBS+ASA, NTG-Placebo+ASA and PBS. In general, all curves overlay at the same range.

ST segment elevation in the group treated with PBS and ASA is higher compared to the PBS control group, but there is no significance as well as between the ASA+NTG-PLACEBO-group. In the ASA+NTG-group ST elevation is decreased compared to the group treated with ASA and PBS.

Figure 10:
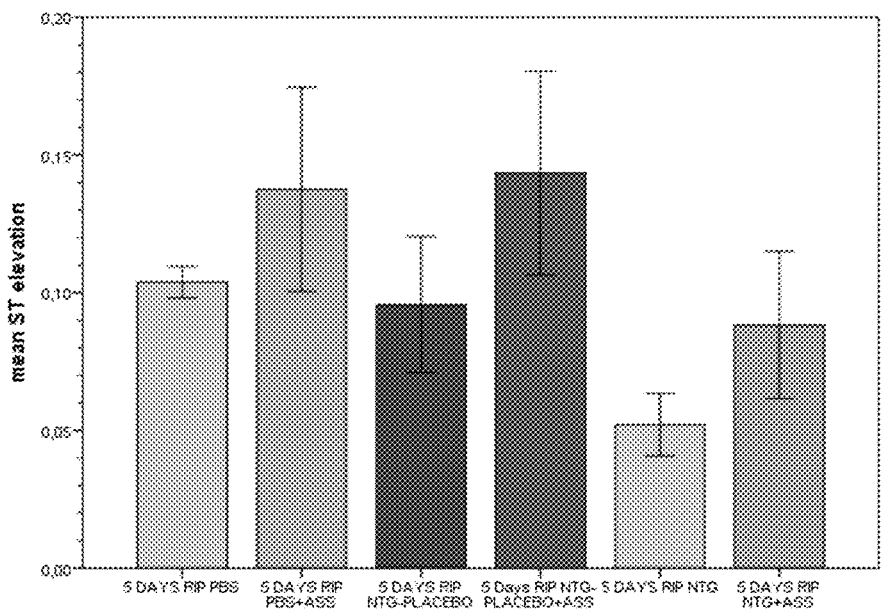

FIG. 10: ST segment elevation (module 4: NO intermittent plus ASA). Column 1 shows 5 DAYS RIP PBS; Column 2 shows 5 DAYS RIP PBS+ASS; Column 3 shows 5 DAYS RIP NTG-PLACEBO; Column 4 shows 5 DAYS RIP NTG-PLACEBO+ASS; Column 5 shows 5 DAYS RIP NTG; Column 6 shows 5 DAYS RIP NTG+ASS; standard deviation is indicated by error bars.

Treatment with NTG+ASA was compared to PBS+ASA, NTG-Placebo+ASA and PBS. Furthermore, all ASA groups (PBS+ASA, NTG-Placebo+ASA, NTG+ASA) were compared to their controls (PBS, NTG-Placebo, NTG). No significant differences were detected.

Figure 11:
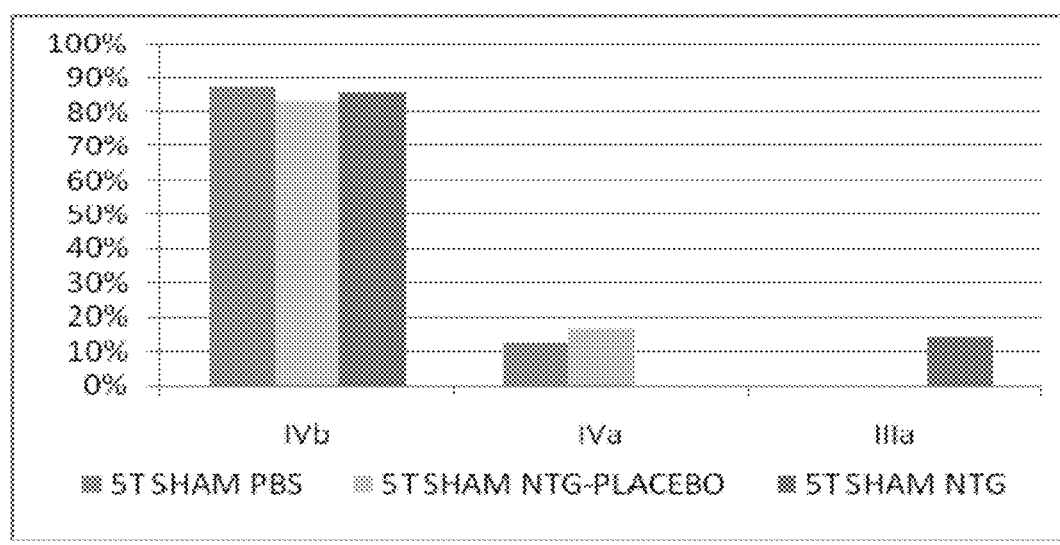

FIG. 11: Arrhythmias during FPO (module 1: Sham Operation (without the RIP)). Numbers of columns are given in consecutive order of the columns in group IVb. Column 1 shows 5 DAYS SHAM PBS; Column 2 shows 5 DAYS SHAM NTG-PLACEBO; Column 3 shows 5 DAYS SHAM NTG.

In accordance with Lown classification, all sham groups were predominantly scaled into grade IVa.

In the "5 DAYS SHAM PBS" group 87.5% of the rats have class IVb arrhythmias and 12.5% class IVa. In the "5 DAYS SHAM NTG-PLACEBO" group 83.3% have IVb arrhythmias and 16.7% class IVa and in the "5 DAYS SHAM NTG" group 85.7% have IVb arrhythmias and 14.3% class IIIa arrhythmias.

Figure 12:
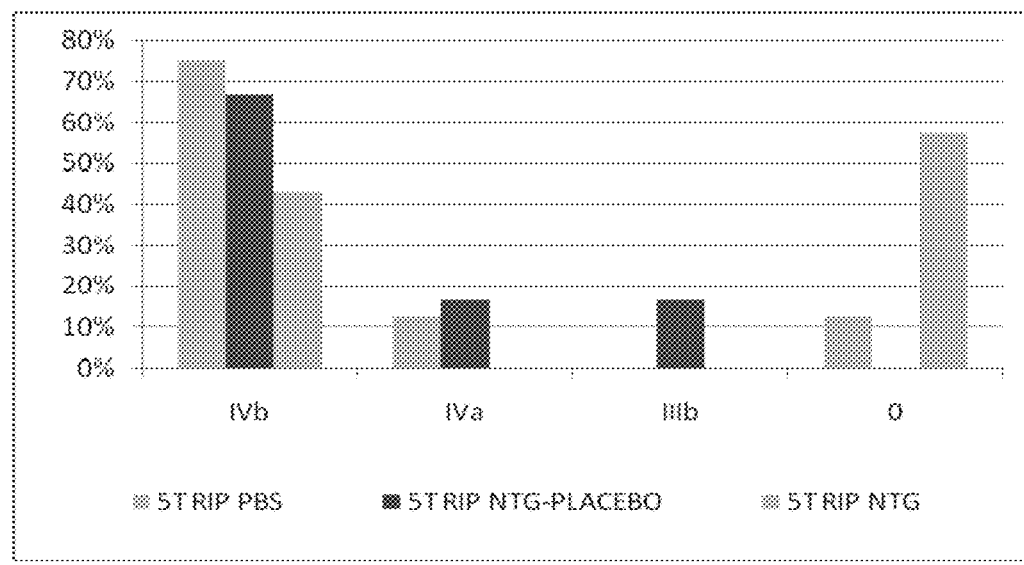

FIG. 12: Arrhythmias during FPO (module 2: NO intermittent (NTG)). Numbers of columns are given in consecutive order of the columns in group IVb. Column 1 shows 5 DAYS RIP PBS; Column 2 shows 5 DAYS RIP NTG-PLACEBO; Column 3 shows 5 DAYS RIP NTG.

While arrhythmias in both control groups, PBS and NTG-Placebo, were predominantly scaled into grade IVa, the NTG treated group was more often scaled into grade 0.

In the "5 DAYS RIP PBS" group, 75.0% of the rats have class IVb arrhythmias, 12.5% IVa and 12.5% class 0. Regarding the "5 DAYS RIP NTG-PLACEBO" group, 66.7% of the rats showed class IVb arrhythmias, 16.7% IVa and 16.7% class IIIb arrhythmias. Interestingly, the "5 DAYS RIP NTG" group shows 42.9% class IVb arrhythmias and 57.1% class 0 arrhythmias.

Figure 13:
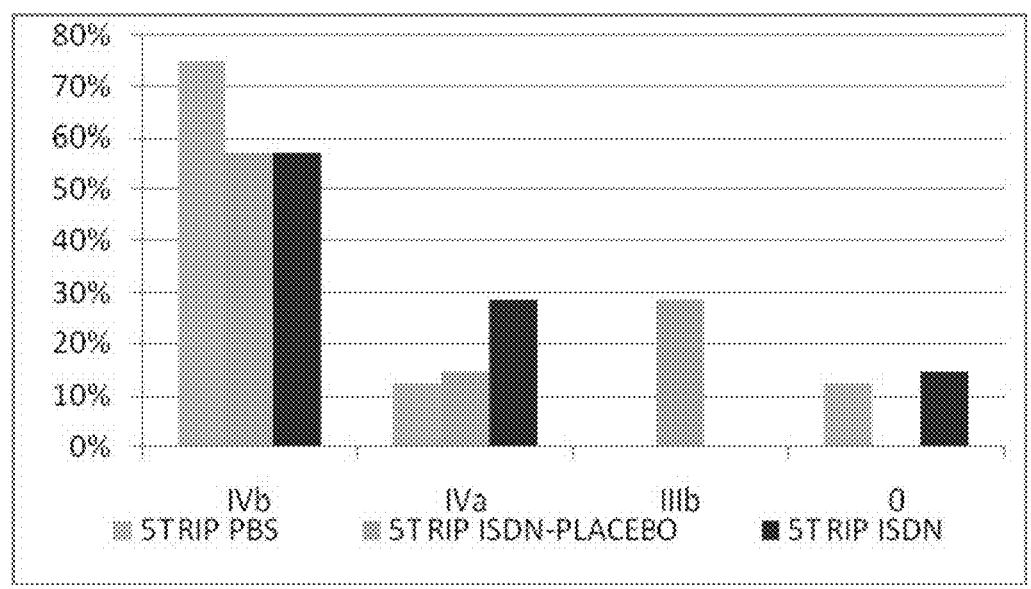

FIG. 13: Arrhythmias during FPO (module 3: NO continuous (ISDN retard)). Numbers of columns are given in consecutive order of the columns in group IVb. Column 1 shows 5 DAYS RIP PBS; Column 2 shows 5 DAYS RIP ISDN-PLACEBO; Column 3 shows 5 DAYS RIP ISDN.

In all groups, arrhythmias were similarly more often scaled into grade IVa.

In the "5 DAYS ISDN-PLACEBO" group, 57.1% of the rats have class IVb arrhythmias, 14.3% class IVa and 28.6% class IIIb. The "5 DAYS RIP ISDN" group shows less severe arrhythmias with 57.1% class IVb, 28.6% class IVa and 14.3% class 0 arrhythmias.

Figure 14:
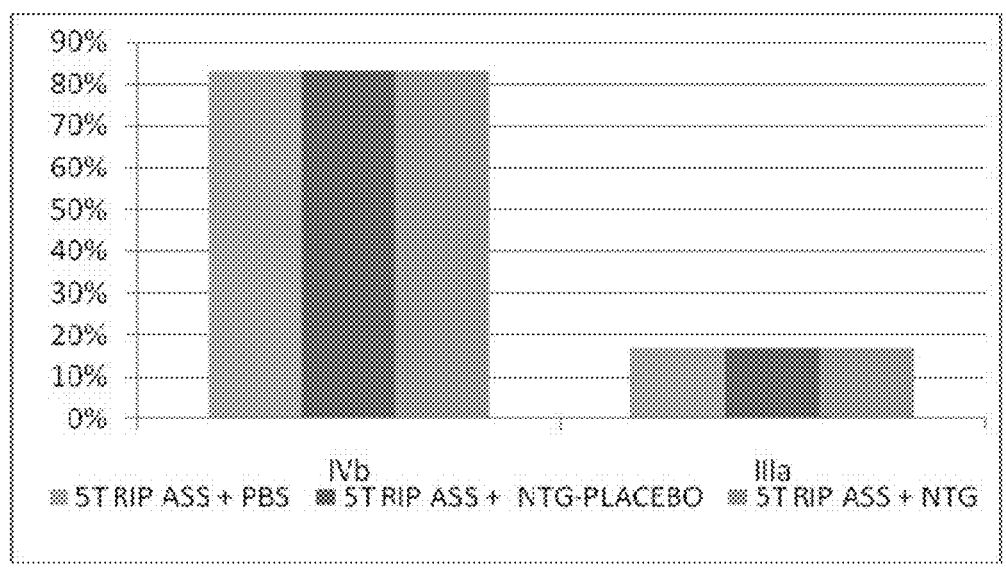

FIG. 14: Arrhythmias during FPO (module 4: NO intermittent plus ASA). Numbers of columns are given in consecutive order of the columns in group IVb. Column 1 shows 5 DAYS RIP ASS+PBS; Column 2 shows 5 DAYS RIP ASS+NTG-PLACEBO; Column 3 shows 5 DAYS RIP ASS+NTG.

Arrhythmias were similarly scaled more into grade IVa in all groups.

In the "5 DAYS RIP ASS+PBS" group, in the group treated with ASS+NTG-PLACEBO and in the "5 DAYS RIP ASS+NTG" group 83.3% of the rats posses class IVb arrhythmias and 16.7% class IIIa.

Figure 15:
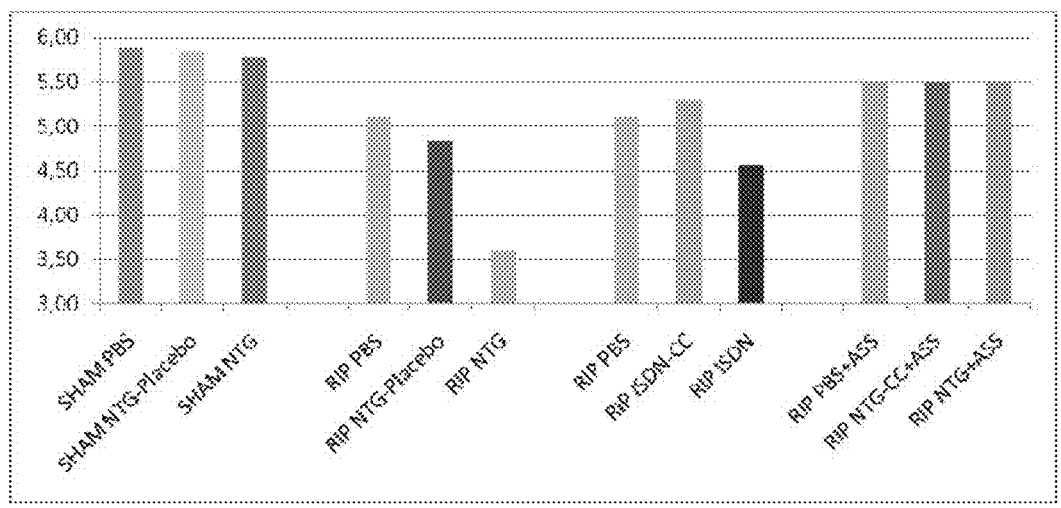

FIG. 15: VPB-Score. Column 1 shows SHAM PBS; Column 2 shows SHAM NTG-Placebo; Column 3 shows SHAM NTG; Column 4 shows RIP PBS; Column 5 shows RIP NTG-Placebo; Column 6 shows RIP NTG; Column 7 shows RIP PBS; Column 8 shows RIP ISDN-CC; Column 9 shows RIP ISDN; Column 10 shows RIP PBS+ASS; Column 11 shows RIP NTG-CC+ASS; Column 12 shows RIP NTG+ASS.

The VBP score shows the percentage of each Lown grade of every group. The Sham-groups have higher VBP-scores. Compared to the group with an ischemic protocol (control group, treated with PBS), more rats show severe arrhythmias. The treatment with NTG reveals reduced arrhythmias, and consequently a lower VPB-Score. The VPB-Score in groups treated with ASA alone or NTG+ASA is higher compared to the controls (treated with PBS).

Regarding the percentage of each Lown grade of every group, a VBP score can be ascertained. The more animals show a higher grade, the higher is the VBP score.

Figure 16:
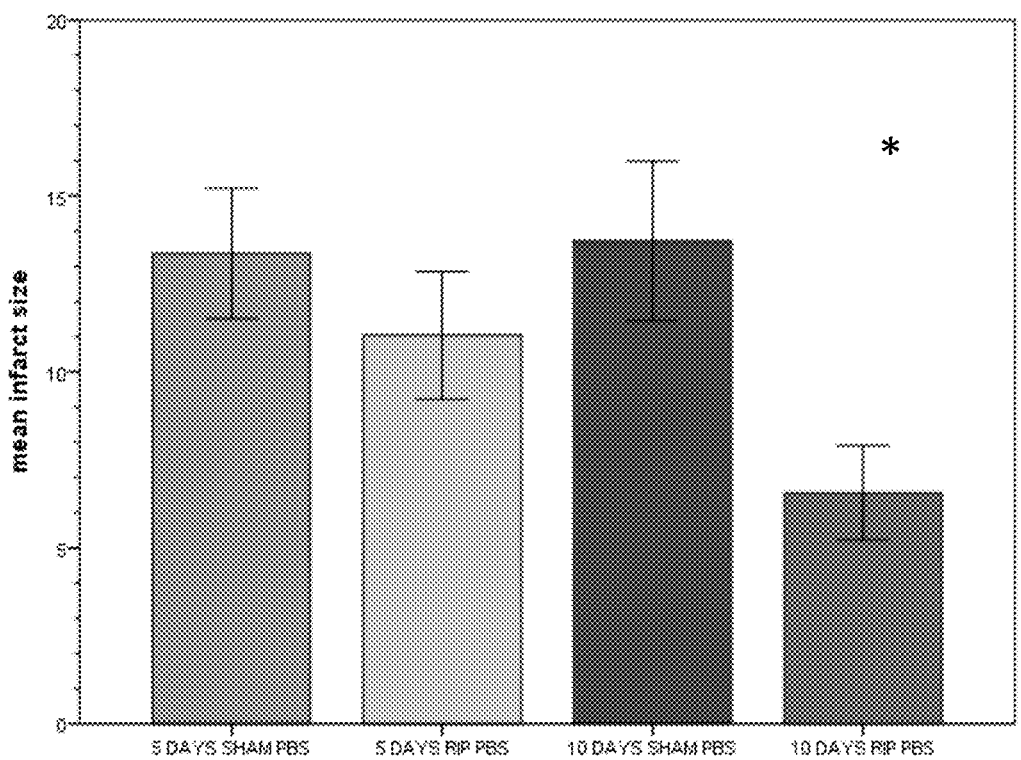

FIG. 16: Infarct size of 5-days and 10-days control-groups. Column 1 shows 5 DAYS SHAM PBS, n=8: 13.36±5.22%; Column 2 shows %; 5 DAYS RIP PBS*=8: 11.05±5.12%; Column 3 shows 10 DAYS SHAM PBS, n=7: 13.71±6.06%; Column 4 shows 10 DAYS RIP PBS, n=6: 6.57±3.26%; standard deviation is indicated by error bars; asterix indicates significant compared to 10 DAYS SHAM PBS (nominal p-value <0.013).

After an ischemic protocol of 5 days there is no significantly smaller infarct size measurable, but after a RIP of 10 days the infracted area is significantly decreased (nominal p-value <0.013).

After 90 minutes of LAD occlusion and 20 minutes reperfusion, infarct size was analyzed. The "10 DAYS RIP PBS" group has a significantly smaller infarct area compared to the "10 DAYS SHAM PBS" group. There is no significance between both 5 DAYS groups.

Figure 17:
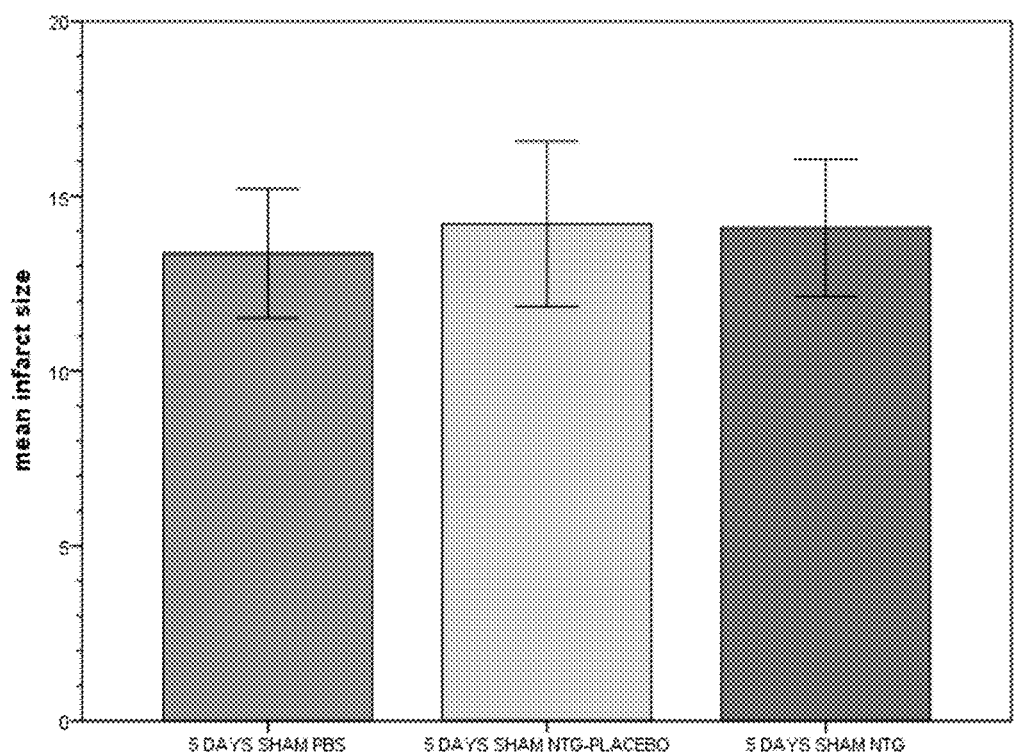

FIG. 17: Infarct size (module 1: Sham Operation (without the RIP)). Column 1 shows 5 DAYS SHAM PBS, n=8: 13.36±5.22 mV; Column 2 shows 5 DAYS SHAM NTG-PLACEBO, n=6: 14.21±5.79 mV; Column 3 shows 5 DAYS SHAM NTG, n=7: 14.09±5.18 mV; standard deviation is indicated by error bars.

The infarct size shows no difference between the SHAM groups.

There is no significance between the three SHAM-groups.

Figure 18:
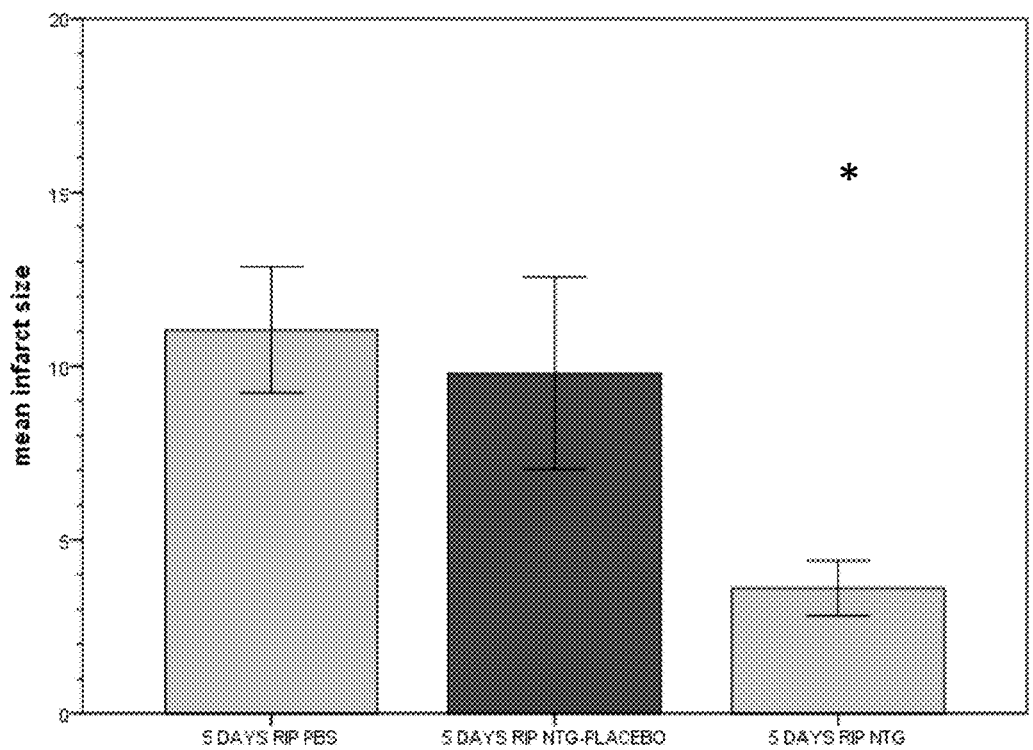

FIG. 18: Infarct size (module 2: NO intermittent (NTG)). Column 1 shows 5 DAYS RIP PBS, n=8: 11.05±5.12%; Column 2 shows 5 DAYS NTG-PLACEBO: n=6; 9.80±6.79 mV; Column 3 shows 5 DAYS RIP NTG, n=7: 3.61±2.08%; standard deviation is indicated by error bars, asterix indicates significant compared to 5 DAYS RIP PBS (nominal p-value <0.017).

The infarct size is significantly smaller after treatment with NTG compared to controls (treated with PBS) (nominal p-value <0.017).

Compared to the "5 DAYS RIP PBS", a significantly smaller infarct area is observed in the "5 DAYS RIP NTG" group. There is no significance between the PBS and NTG-PLACEBO-group.

Figure 19:
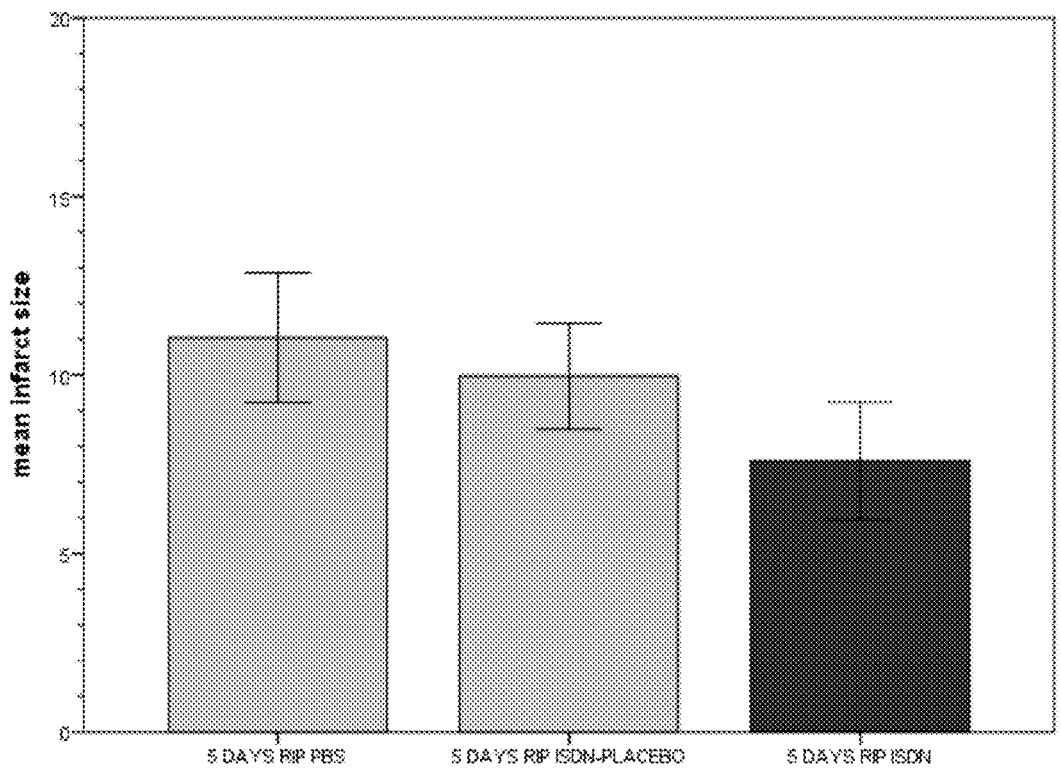

FIG. 19: Infarct size (module 3: NO continuous (ISDN retard)). Column 1 shows 5 DAYS RIP PBS, n=8: 11.05±5.12%; Column 2 shows 5 DAYS ISDN-PLACEBO, n=6: 9.97±3.65%; Column 3 shows 5 DAYS RIP ISDN, n=7: 7.59±4.38%; standard deviation is indicated by error bars.

The infarct size after treatment with ISDN is smaller compared to controls (treated with PBS or ISDN-Placebo), but there is no significance.

The infarct size in the ISDN group ("5 DAYS RIP ISDN") is smaller compared to the PBS group, as well as the ISDN-PLACEBO-group.

Figure 20:
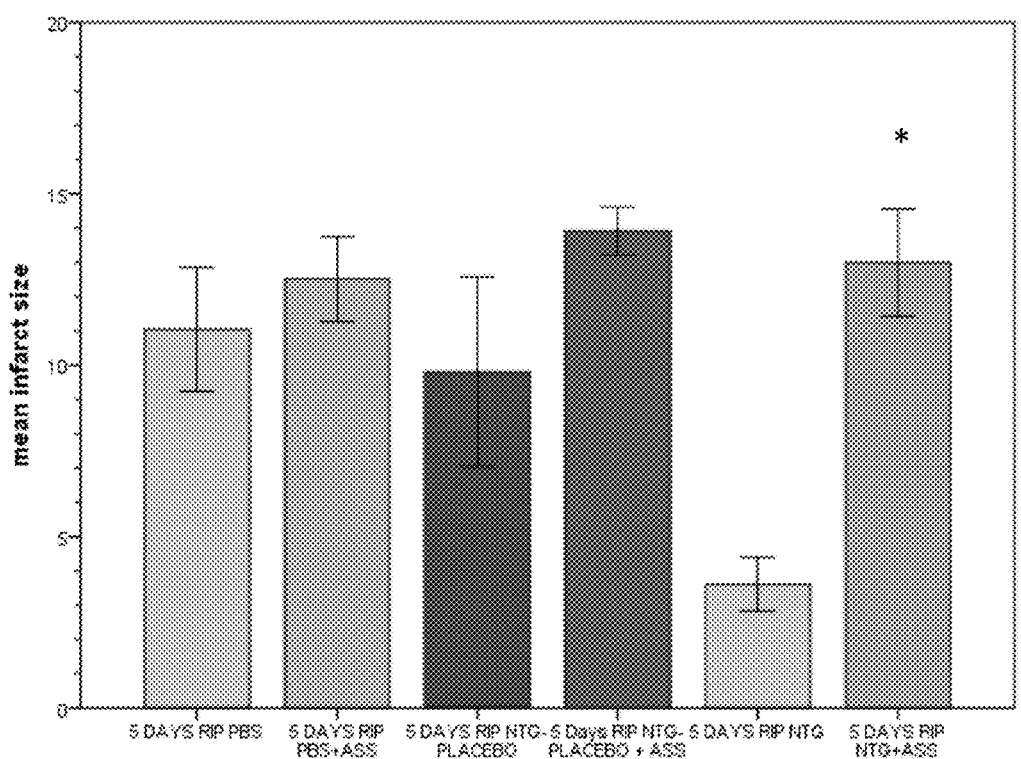

FIG. 20: infarct size (module 4: NO intermittent plus ASS). Column 1 shows 5 DAYS RIP PBS, n=8; 11.05±5.12%; Column 2 shows 5 DAYS RIP ASS+PBS, n=6: 12.51±3.05%; Column 3 shows 5 DAYS NTG-PLACEBO: n=6; 9.80±6.79%; Column 4 shows 5 DAYS RIP NTG-PLACEBO+ASS, n=6: 13.92±1.71%; Column 5 shows 5 DAYS RIP NTG, n=7: 11.05±5.12%; Column 6 shows 5 DAYS RIP NTG+ASS, n=6: 13.00±3.82%; standard deviation is indicated by error bars, asterix indicates significant compared to 5 DAYS RIP NTG (nominal p-value <0.017).

The infarct size after treatment with NTG plus ASS is significantly increased compared to the treatment with NTG alone (nominal p-value <0.017).

The infarct size in the group treated with ASA ("5 DAYS ASS+PBS") is minimally increased compared to the PBS control group, as well as the ASS+NTG-PLACEBO-group. There is no difference between the ASS+NTG-group and the group treated with ASS and PBS. However, the infarct area in the NTG group is significantly smaller compared to the ASA+NTG group.

Figure 21:
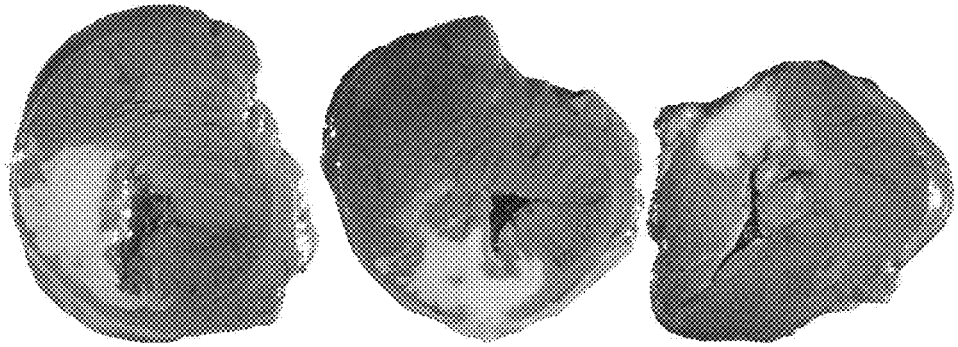
Figure 21:
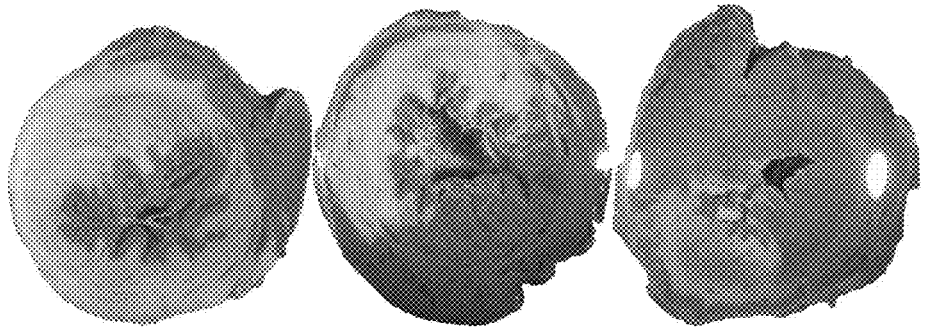
Figure 21:
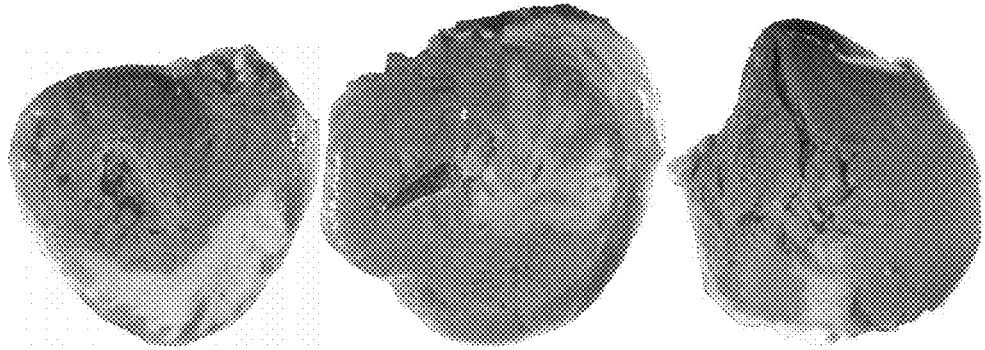
Figure 21:
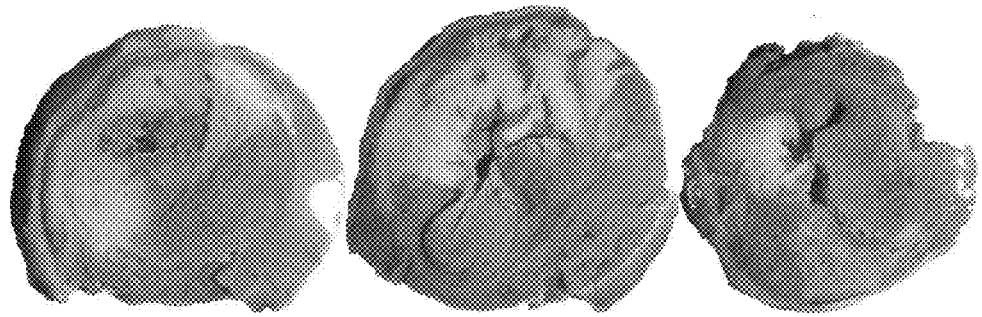
Figure 21:
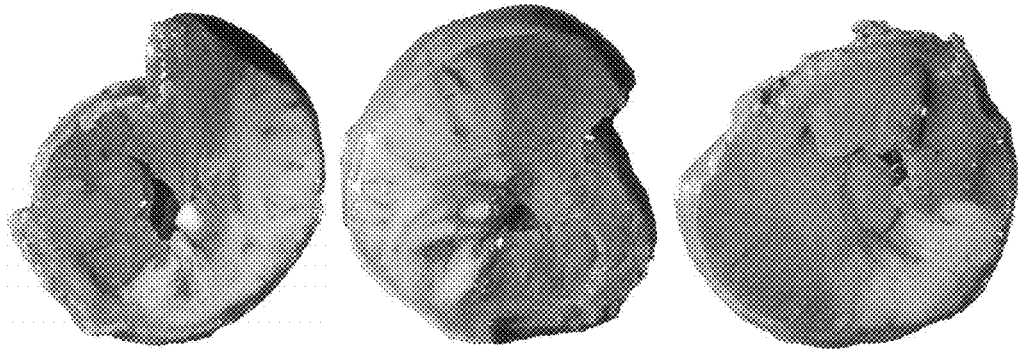
Figure 21:
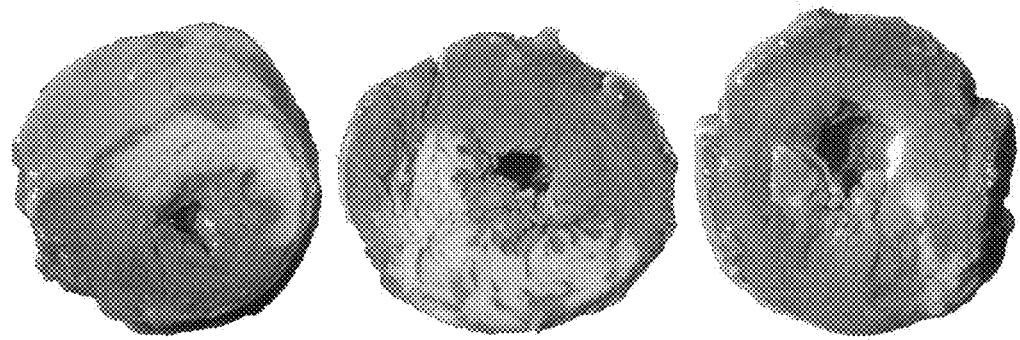
Figure 21:
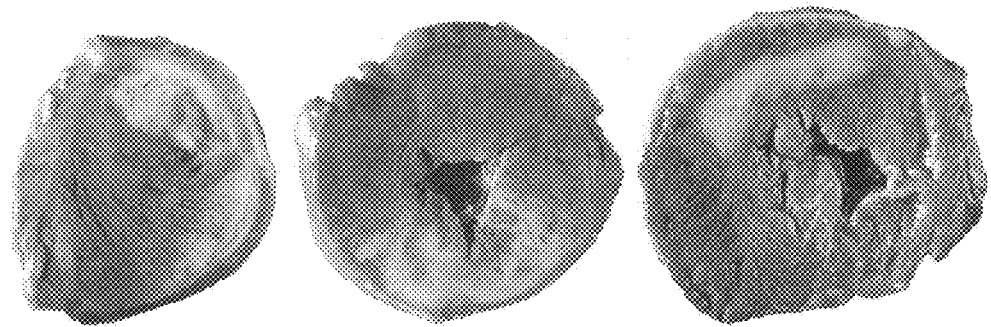
Figure 21:
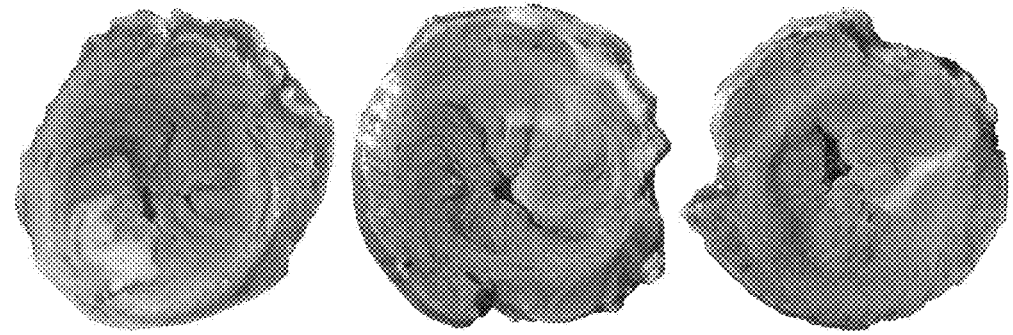
Figure 21:
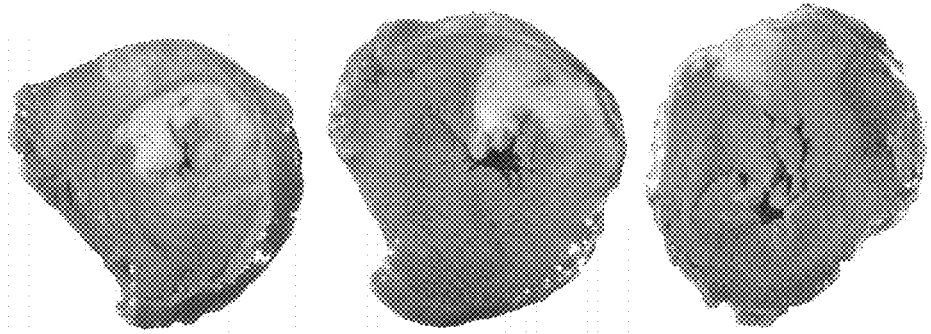
Figure 21:
Figure 21:
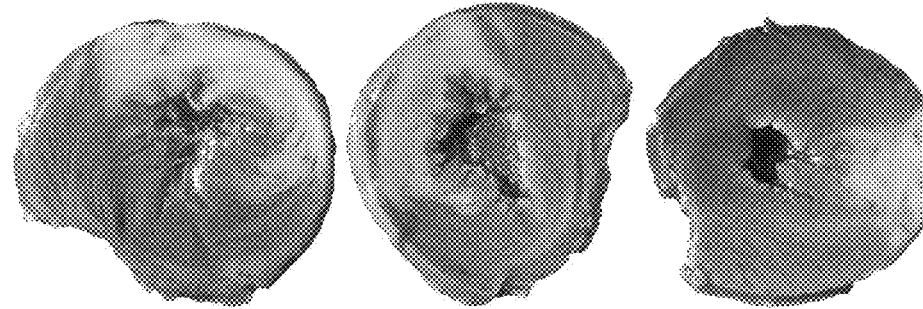
Figure 21:
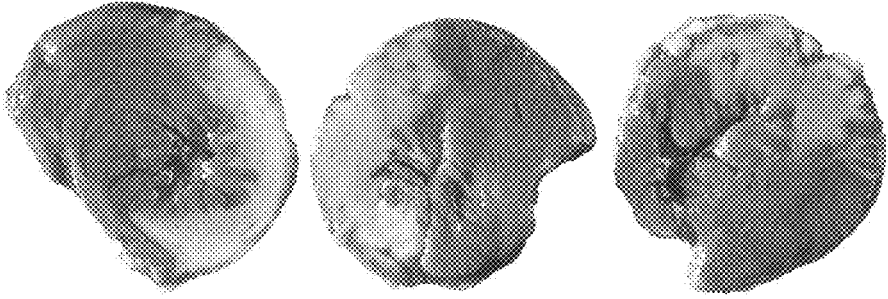
Figure 21:
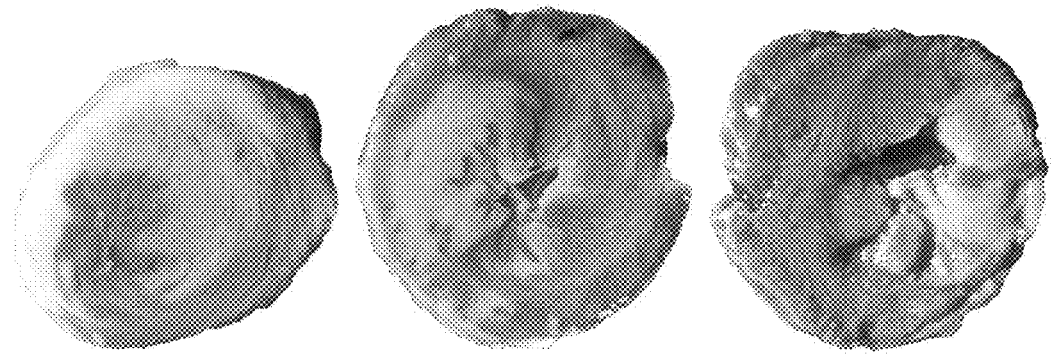

FIG. 21: TTC-staining. The pictures shows slices of three levels. Infarcted tissue stains a pale-white since they lack the enzymes with which the TTC reacts. Thus the areas of necrosis are clearly discernible and quantifiable.

Figure 22:
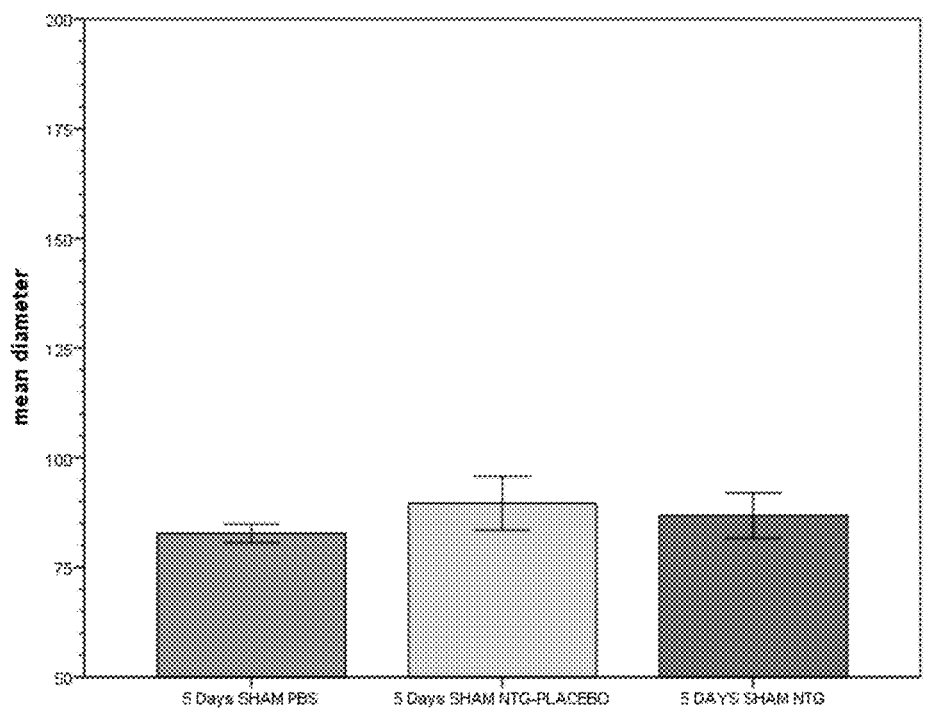

FIG. 22: collateral diameters of ROI (module 1: Sham Operation (without the RIP)). Column 1 shows 5 DAYS SHAM PBS, n=3: 82.7±3.7 µm; Column 2 shows 5 DAYS SHAM NTG-PLACEBO, n=3: 89.6 µm±10.6 µm; Column 3 shows 5 DAYS SHAM NTG, n=3: 86.8±9.0 µm; standard deviation is indicated by error bars.

There is no growth of collaterals and no differences measurable between the SHAM groups.

There is no significance between the three SHAM-groups.

Figure 23:
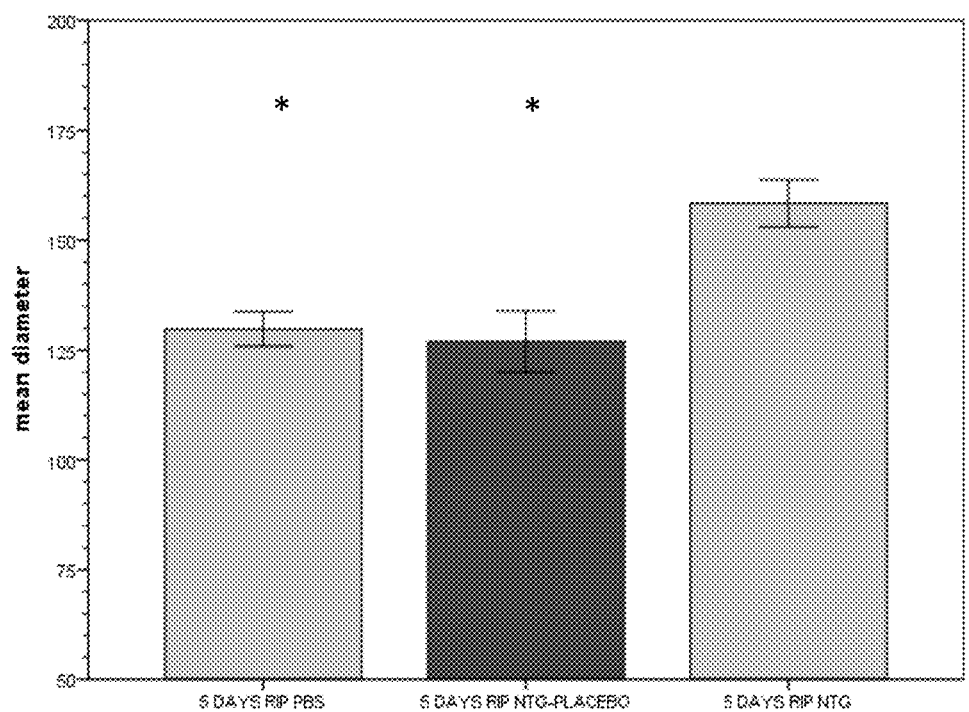

FIG. 23: collateral diameters of ROI (module 2: NO intermittent (NTG)). Column 1 shows 5 DAYS RIP PBS, n=3: 129.8±6.9 µm; Column 2 shows 5 DAYS RIP NTG-PLACEBO: n=3; 127.0±12.1 µm; Column 3 shows 5 DAYS RIP NTG, n=3: 158.4±9.2 µm; standard deviation is indicated by error bars, asterix indicates significant compared to 5 DAYS RIP NTG (nominal p-value <0.033).

Diameters of collaterals are significantly increased by treatment with NTG compared to controls (treated with PBS or NTG-Placebo) (nominal p-value <0.033).

Compared to the "5 DAYS RIP PBS", the diameters of the collaterals in the ROI in the "5 DAYS RIP NTG" group are significantly increased. There is no difference between the PBS and NTG-PLACEBO-group.

Figure 24:
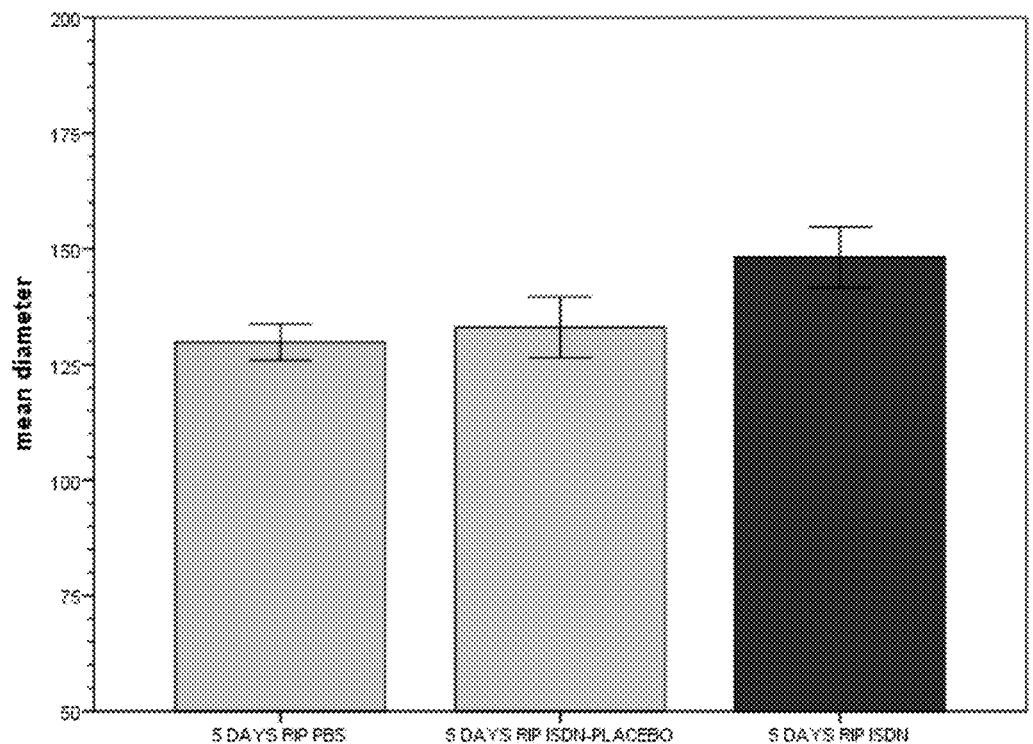

FIG. 24: collateral diameters of ROI (module 3: NO continuous (ISDN retard)). Column 1 shows 5 DAYS RIP PBS, n=3: 129.8±6.9 µm; Column 2 shows 5 DAYS ISDN-PLACEBO, n=3: 133.0±11.5 µm; Column 3 shows 5 DAYS RIP ISDN, n=3: 148.2±11.3 µm; standard deviation is indicated by error bars.

No differences are measurable in the diameter of collaterals after treatment with ISDN or ISDN-Placebo.

The diameters of the collaterals in the ISDN group ("5 DAYS RIP ISDN") are enhanced compared to the PBS group, as well as compared to the ISDN-PLACEBO group.

Figure 25:
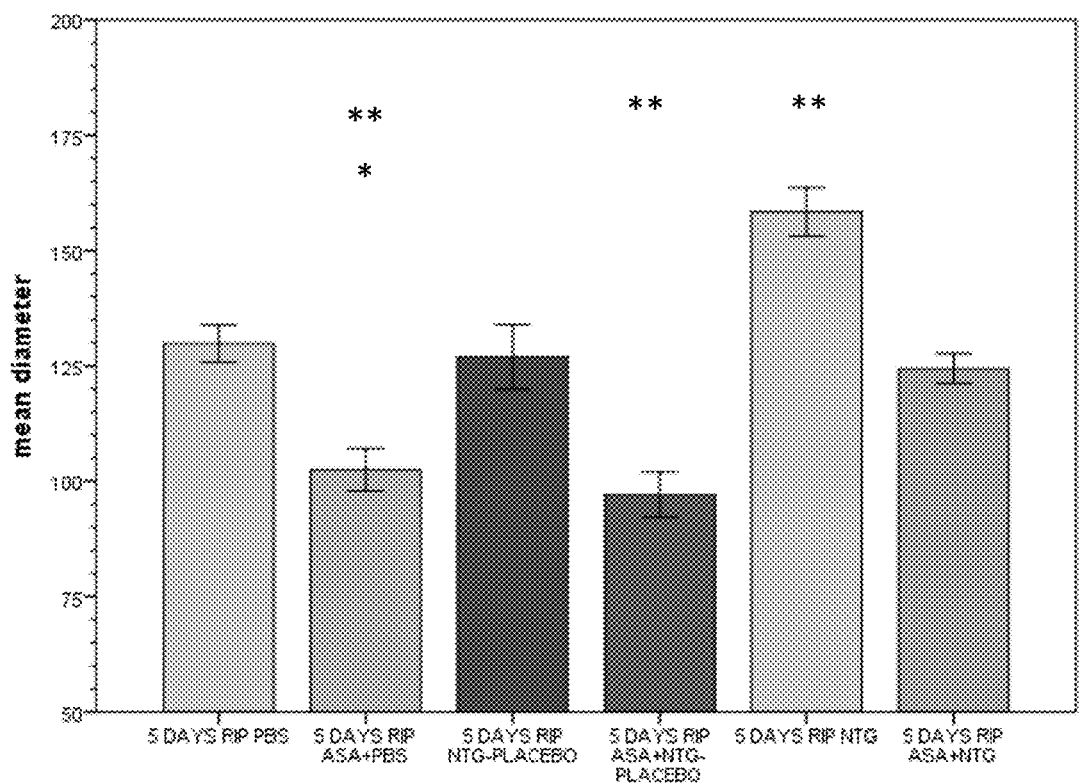

FIG. 25: Collateral diameter of ROI (module 4: NO intermittent plus ASA). Column 1 shows 5 DAYS RIP PBS, n=3; 129.8±6.9 µm; Column 2 shows 5 DAYS RIP PBS+ASS, n=3: 102.5±8.0 µm; Column 3 shows 5 DAYS RIP NTG-PLACEBO: n=3; 127.0±12.1 µm; Column 4 shows 5 DAYS NTG-PLACEBO+ASS, n=3: 97.1±8.61 µm; Column 5 shows 5 DAYS RIP NTG, n=3: 158.4±9.2 µm; Column 6 shows 5 DAYS RIP ASS+NTG, n=3: 124.4±5.6 µm; standard deviation is indicated by error bars, one asterix indicates significant compared to 5 DAYS RIP PBS (nominal p-value <0.039); two asterix indicate significant compared to 5 DAYS RIP ASS+NTG (nominal p-value <0.039).

Diameters of collaterals are significantly smaller after treatment with ASA compared to controls (treated with PBS). An additional treatment with NTG abolished the inhibiting effect of ASS. NTG-treatment alone shows significantly increased diameter compared to controls (treated with PBS) (nominal p-value <0.039).

The diameter in the group treated with PBS and ASS are significantly smaller compared to the PBS control group as well as the ASS+NTG-PLACEBO-group, but there is no significance. In the ASA+NTG-group diameter are increased compared to the group treated with PBS and ASA.

Figure 26:

FIG. 26: MicroCT imaging of the "ROI": (A) "5DAYS SHAM PBS"; (B) "5DAYS SHAM NTG"; (C) "5DAYS RIP ISDN"; (D) "5DAYS RIP PBS"; (E) "5DAYS RIP NTG"; (F) "5DAYS RIP ASS+PBS; (G) "5DAYS RIP ASS+NTG".

The pictures show the growth of the collateral diameter in the region of interest by the ischemic protocoll treated with PBS (D), NTG (E), or ISDN (C) compared to SHAM treated with PBS (A) or NTG (B), Inhibition of collateral growth by treatment with ASA (F) is partially abolished by additional treatment with NTG (G).

Figure 27:
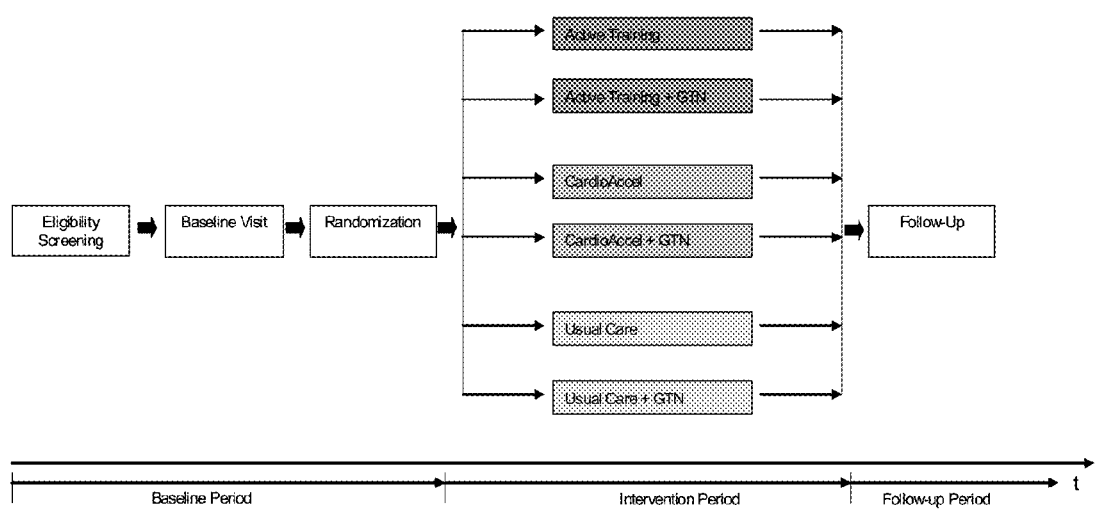

FIG. 27: Study Flow Chart. Duration of the baseline period is estimated to be approximately 2 weeks. Duration of the intervention period will be six weeks. The follow up period will include an immediate investigation (one day up to maximal three days after the intervention period) and a long-term follow up investigation (1 month after intervention period).

DETAILED DESCRIPTION

Examples

The following Examples illustrate inter alia the production of various formulations according to the invention without reducing the scope of the invention to these Examples.

Comparative Example 1

Commercially available GTN tablets each with a total weight of 35 mg, containing 0.4 mg GTN and lactose monohydrate, glycerol monostearate, pre-agglutinated starch, calcium stearate and colloidal silicon dioxide as excipients, were packaged individually in film stick packs and stored at 40° C./75% rel humidity for three months.

Comparative Example 2

| Contents | Quantity [g] |
| --- | --- |
| GTN in diluent lactose monohydrate 10% | 0.60 |
| Polyethylene glycol 400 | 0.36 |
| Isomalt | 16.81 |
| Xylitol | 12.01 |
| Silicon dioxide (Aeroperl ®) | 0.25 |
| Total | 30.03 |
| GTN concentration | 0.20% |

The active substance triturate was mixed well with the liquid polyethylene glycol; the other substances were added in the sequence listed above and mixed. 200-mg portions of the free-flowing powder were filled in stick packs and stored at 40° C./75% rel humidity for three months.

Example 1

| Contents | Quantity [g] |
| --- | --- |
| GTN (5%) in diluent MCT | 1.033 |
| Triethyl citrate | 1.032 |
| Isomalt | 16.513 |
| Xylitol | 6.248 |
| Silicon dioxide (Aeroperl ®) | 0.207 |
| Total | 25.033 |
| GTN concentration | 0.207% |

Triethyl citrate was mixed with GTN phlegmatized in a diluent of medium chain triglycerides (MCT). The solution was mixed well with the isomalt. Then xylitol and finally silicon dioxide were added and mixing was continued. 200-mg portions of the free-flowing powder were filled in stick packs and stored at 40° C./75% rel humidity for three months.

The GTN concentration was quantified after production and at various points during storage using HPLC analysis. The individual doses were dissolved in a suitable solvent to perform the analysis. The GTN was detected using a UV-VIS detector at a wavelength of 225 nm.

| GTN concentration following storage at 40° C./75% rel. humidity | | | | |
| --- | --- | --- | --- | --- |
| Product according to | 0 months | 2 weeks | 1 month | 3 months |
| Comp. example 1 | 0.391 mg | 0.079 mg | 0.065 mg | * |
| Comp. example 2 | 0.407 mg | n.c. | 0.305 mg | 0.245 mg |
| Example 1 | 0.415 mg | n.c. | n.c. | 0.394 mg |

*The test was terminated after one month because more than 80% of the active substance had already been lost.
n.c.—not conducted This initial comparative test proves that neither the commercially available tablet, nor a powder mixture with the substances contained in a conventional tablet, nor a preparation with polyethylene glycol is suitably stable in a stick pack. The only acceptable level of storage stability was achieved with the addition of the stabilizing ester according to the invention together with a GTN concentrate phlegmatized in MCT as a liquid.

Example 2

| Contents | Quantity [g] |
| --- | --- |
| GTN (5%) in diluent MCT | 2.00 |
| TPGS | 1.00 |
| Magnesium aluminometasilicate | 2.50 |
| Isomalt | 44.5 |
| Total | 50.00 |
| GTN concentration | 0.20% |

TPGS was melted at 50° C. and mixed with GTN concentrate in a diluent of MCT. While still warm, the mixture was blended well with the magnesium aluminometasilicate. Then isomalt was added and mixing was continued. 200-mg portions of the free-flowing powder were filled in stick packs and stored at 25° C./60% rel. humidity. The GTN concentration was quantified immediately after production and at various points during storage as disclosed under Example 1. The results are presented in the following table:

| | Storage duration/temp. | | |
| --- | --- | --- | --- |
| | 0 months | 3 months/25° C. | 6 months/25° C. |
| GTN concentration | 0.400 mg | 0.398 mg | 0.392 mg |

Example 3

| Contents | Quantity [g] |
| --- | --- |
| GTN (5%) in diluent MCT | 2.02 |
| Glycerol monocaprylocaprate Ph. Eur. | 0.52 |
| Magnesium aluminometasilicate | 1.50 |
| Isomalt | 45.99 |
| Total | 50.03 |
| GTN concentration | 0.20% |

The glycerol monocaprylocaprate was melted at 40° C. and mixed with a GTN concentrate in MCT diluent. While still warm, the mixture was blended well with the magnesium aluminometasilicate. Then isomalt was added and mixing was continued. 200-mg portions of the free-flowing powder were filled in stick packs and stored at 40° C./75% rel humidity and at 25° C./60% rel. humidity. The GTN concentration was quantified immediately after production and at various points during storage as disclosed under Example 1. The results are presented in the following table:

|  | Storage duration/temp. | | |
| --- | --- | --- | --- |
|  | 0 months | 6 months/25° C. | 6 months/40° C. |
| GTN concentration | 0.397 mg | 0.383 mg | 0.355 mg |

Example 4

| Contents | Quantity [g] |
| --- | --- |
| GTN (5%) in diluent MCT | 79.35 |
| Glycerol monocaprylocaprate Ph. Eur. | 19.85 |
| Anhydrous dibasic calcium phosphate | 100.80 |
| Isomalt | 1800.00 |
| Total | 2000.00 |
| GTN concentration | 0.2% |

The glycerol monocaprylocaprate was melted at 40° C. and mixed with a GTN concentrate in a MCT diluent. While still warm, the mixture was blended well with the anhydrous dibasic calcium phosphate. Then isomalt was added and mixing was continued. 200-mg portions of the free-flowing powder were filled in stick packs and stored at 40° C./75% rel. humidity and at 25° C./60% rel. humidity. The GTN concentration was quantified immediately after production and at various points during storage as disclosed under Example 1. The results are presented in the following table:

|  | Storage duration | | |
| --- | --- | --- | --- |
|  | 0 months | 3 months | 6 months |
| GTN concentration at 40° C. | 0.380 mg | 0.380 mg | 0.383 mg |
| GTN concentration at 25° C. | 0.380 mg | 0.380 mg | 0.379 mg |

Comparative example 3

| Contents | Quantity [g] |
| --- | --- |
| GTN (5%) in diluent MCT | 1.193 |
| Anhydrous dibasic calcium phosphate | 1.513 |
| Isomalt | 19.80 |
| Xylitol | 7.50 |
| Total | 30.006 |
| GTN concentration | 0.2% |

GTN concentrate in MCT diluent was blended well with the anhydrous dibasic calcium phosphate. Then isomalt and xylitol were added and mixing was continued. 200-mg portions of the free-flowing powder were filled in stick packs and stored at 40° C./75% rel. humidity and at 25° C./60% rel. humidity. The GTN concentration was quantified immediately after production and at various points during storage as disclosed under Example 1. The results are presented in the following table:

|  | Storage duration | |
| --- | --- | --- |
|  | 0 months | 3 months |
| GTN concentration at 40° C. | 0.410 mg | 0.340 mg |
| GTN concentration at 25° C. | 0.410 mg | 0.363 mg |

A comparison between the data from Example 4 according to the invention and the non-stabilized preparation according to comparative Example 3 reveals that a clinically significant average loss of 17% and 11% occurred without stabilization after a storage period of three months at 40° C. and 25° C., respectively. A product having this degree of susceptibility to deterioration and loss of active ingredient is not suitable commercially for sale as a pharmaceutical. In sharp contrast, the content of the active substance in Example 4 remained nearly constant for six months when in the presence of a stabilizer in accordance with the present invention.

The following Examples illustrate further the benefit of stabilized formulas according to the invention. Additionally, the following Examples demonstrate the benefits of mixtures of the stabilizers as contemplated by the present invention. Importantly, the following Examples illustrate stabilization obtained at even more elevated temperatures, i.e., 50° C.:

Example 5

| Contents | Quantity [g] |
| --- | --- |
| GTN (5%) in diluent MCT | 43.9 |
| Glycerol monocaprylocaprate Ph. Eur. | 16.6 |
| TPGS | 16.6 |
| Magnesium aluminometasilicate | 54.9 |
| Isomalt | 957.0 |
| Peppermint flavoring agent | 11.0 |
| Total | 1100.00 |
| GTN concentration | 0.2% |

The glycerol monocaprylocaprate and TPGS were melted at 50° C. and mixed with GTN concentrate in MCT diluent. While still warm, the mixture was blended well with the magnesium aluminometasilicate. Then isomalt and peppermint flavoring agent were added and mixing was continued. 200-mg portions of the free-flowing powder were filled in stick packs and stored at 50° C. and at 40° C./75% rel. humidity. The GTN concentration was quantified immediately after production and at various points during storage as disclosed under Example 1.

Example 6

| Contents | Quantity [g] |
| --- | --- |
| GTN (5%) in diluent MCT | 40.0 |
| Solid Triglycerides | 20.0 |
| Anhydrous dibasic calcium phosphate | 49.9 |
| Isomalt | 880.1 |
| Peppermint flavoring agent | 10.0 |
| Total | 1000.00 |
| GTN concentration | 0.2% |

The solid triglycerides were melted at 50° C. and mixed with GTN concentrate in MCT diluent. While still warm, the mixture was blended well with the anhydrous dibasic calcium phosphate. Then isomalt was added in portions followed by the peppermint flavoring agent and mixing was continued. 200-mg portions of the free-flowing powder were filled in stick packs and stored at 50° C. and at 40° C./75% rel. humidity. The GTN concentration was quantified immediately after production and at various points during storage as disclosed under Example 1.

Example 7

| Contents | Quantity [g] |
| --- | --- |
| GTN (5%) in diluent MCT | 40.0 |
| Solid Triglycerides | 10.0 |
| Glycerol monocaprylocaprate Ph. Eur. | 10.0 |
| Anhydrous dibasic calcium phosphate | 50.0 |
| Isomalt | 880.0 |
| Peppermint flavoring agent | 10.0 |
| Total | 1000.00 |
| GTN concentration | 0.2% |

The solid triglycerides and glycerol monocaprylocaprate were melted at 50° C. and mixed with a GTN concentrate in MCT diluent. While still warm, the mixture was blended well with the anhydrous dibasic calcium phosphate. Then isomalt was added in portions followed by the peppermint flavoring agent and mixing was continued. 200-mg portions of the free-flowing powder were filled in stick packs and stored at 50° C. and at 40° C./75% rel. humidity. The GTN concentration was quantified immediately after production and at various points during storage as disclosed under Example 1.

Example 8

| Contents | Quantity [g] |
| --- | --- |
| GTN (5%) in diluent MCT | 40.0 |
| Oleoyl macrogol-6-glycerides | 20.0 |
| Anhydrous dibasic calcium phosphate | 50.0 |
| Isomalt | 880.0 |
| Peppermint flavoring agent | 10.0 |
| Total | 1000.00 |
| GTN concentration | 0.2% |

The oleoyl macrogol-6-glycerides were mixed with GTN in MCT. The mixture was blended well with the anhydrous dibasic calcium phosphate. Then isomalt was added in portions followed by the peppermint flavoring agent and mixing was continued. 200-mg portions of the free-flowing powder were filled in stick packs and stored at 50° C. and at 40° C./75% rel. humidity. The GTN concentration was quantified immediately after production and at various points during storage as disclosed under Example 1.

Example 9

| Contents | Quantity [g] |
| --- | --- |
| GTN (5%) in diluent MCT | 40.0 |
| Glycerol monooleate | 20.0 |
| Anhydrous dibasic calcium phosphate | 50.0 |
| Isomalt | 880.0 |
| Peppermint flavoring agent | 10.0 |
| Total | 1000.00 |
| GTN concentration | 0.2% |

The glycerol monooleate was melted at 50° C. and mixed with a GTN concentrate in MCT diluent. The mixture was blended well with the anhydrous dibasic calcium phosphate. Then isomalt was added in portions followed by the peppermint flavoring agent and mixing was continued. 200-mg portions of the free-flowing powder were filled in stick packs and stored at 50° C. and at 40° C./75% rel. humidity. The GTN concentration was quantified immediately after production and at various points during storage as disclosed under Example 1.

The results from the storage tests with the preparations from Examples 5-9 are presented in the following table:

| | Storage duration at 50° C. | | |
| --- | --- | --- | --- |
| | 0 months | 1 month | 2 months |
| Example 5 | 0.404 mg | 0.380 mg | 0.369 mg |
| Example 6 | 0.394 mg | 0.390 mg | 0.384 mg |
| Example 7 | 0.391 mg | 0.393 mg | 0.389 mg |
| Example 8 | 0.394 mg | 0.392 mg | 0.388 mg |
| Example 9 | 0.390 mg | 0.376 mg | 0.377 mg |

Taken together the results unambiguously show that loss of GTN is significantly reduced through the addition of a non-volatile ester stabilizer as compared with the stabilizer-free composition from comparative Examples 2 and 3.

Example 10

| Contents | Quantity [g] |
| --- | --- |
| GTN (5%) in diluent MCT | 40.0 |
| Oleoyl macrogol-6-glycerides | 10.0 |
| Triglycerides | 10.0 |
| Anhydrous dibasic calcium phosphate | 50.0 |
| Isomalt | 880.0 |
| Peppermint flavoring agent | 10.0 |
| Total | 1000.0 |
| GTN concentration | 0.2% |

Oleoyl macrogol-6-glycerides and triglycerides were mixed with GTN phlegmatized in MCT. The mixture was blended well with the anhydrous dibasic calcium phosphate. Then isomalt was added in portions followed by the peppermint flavoring agent and mixing was continued. 200-mg portions of the free-flowing powder were filled in stick packs and stored at 50° C. and at 40° C./75% rel. humidity.

Example 11

| Contents | Quantity [g] |
| --- | --- |
| GTN (5%) in diluent MCT | 40.0 |
| Glycerol monooleate | 10.0 |

-continued

| Contents | Quantity [g] |
| --- | --- |
| Mono- and Diglycerides | 10.0 |
| Anhydrous dibasic calcium phosphate | 50.0 |
| Isomalt | 880.0 |
| Peppermint flavoring agent | 10.0 |
| Total | 1000.0 |
| GTN concentration | 0.2% |

Glycerol monooleate and mono- and diglycerides (type Geleol) were melted at 50° C. and mixed with a GTN concentrate in a MCT diluent. The mixture was blended well with the anhydrous dibasic calcium phosphate. Then isomalt was added in portions followed by the peppermint flavoring agent and mixing was continued. 200-mg portions of the free-flowing powder were filled in stick packs and stored at 50° C. and at 40° C./75% rel. humidity.

Example 12

| Contents | Quantity [g] |
| --- | --- |
| GTN (5%) in diluent MCT | 40.1 |
| Myristyl lactate | 20.0 |
| Anhydrous dibasic calcium phosphate | 50.0 |
| Isomalt | 879.9 |
| Peppermint flavoring agent | 10.1 |
| Total | 1000.1 |
| GTN concentration | 0.2% |

Myristyl lactate was mixed with a GTN concentrate in MCT diluent. The mixture was blended well with the anhydrous dibasic calcium phosphate. Then isomalt was added in portions followed by the peppermint flavoring agent and mixing was continued. 200-mg portions of the free-flowing powder were filled in stick packs and stored at 50° C. and at 40° C./75% rel. humidity.

Example 13

| Contents | Quantity [g] |
| --- | --- |
| GTN (5%) in diluent propylene glycol | 4.0 |
| Glycerol monocaprylocaprate Ph. Eur. | 1.0 |
| Anhydrous dibasic calcium phosphate | 5.0 |
| Isomalt | 89.0 |
| Peppermint flavoring agent | 1.0 |
| Total | 100.00 |
| GTN concentration | 0.2% |

GTN concentrate in propylene glycol diluent was blended well with the anhydrous dibasic calcium phosphate. In a separate vessel the glycerol monocaprylocaprate was melted at 40° C. and added to the absorbed diluted GTN. Then isomalt was added in portions followed by the peppermint flavoring agent and mixing was continued. 200-mg portions of the free-flowing powder were filled in stick packs and stored at 50° C. and at 40° C./75% rel. humidity.

Example 14

| Contents | Quantity [g] |
| --- | --- |
| GTN (5%) in diluent propylene glycol | 4.0 |
| Oleoyl macrogol-6-glycerides | 2.0 |
| Anhydrous dibasic calcium phosphate | 5.0 |
| Isomalt | 88.0 |
| Peppermint flavoring agent | 1.0 |
| Total | 100.0 |
| GTN concentration | 0.2% |

GTN concentrate in propylene glycol diluent was blended well with the anhydrous dibasic calcium phosphate, oleoyl macrogol-6-glycerides were added to the absorbed diluted GTN. Then isomalt was added in portions followed by the peppermint flavoring agent and mixing was continued. 200-mg portions of the free-flowing powder were filled in stick packs and stored at 50° C. and at 40° C./75% rel. humidity.

It is expected that the GTN-containing formulations of Examples 10-14 will again demonstrate the advantages of the inclusion of a stabilizer in the above-described GTN absorbate compositions even when held at stressful storage temperatures such as 50° C.

As described elsewhere herein, the preparations exemplified above according to the invention can be supplied as a single dose in the form of a stick pack, a capsule or a sachet. In addition, it is possible to manufacture tablets, mini-tablets or pellets for oromucosal or sublingual administration from the stabilized powders or granules, as necessary, following the addition of other fillers, disintegrants, glidants, binders, and lubricants using routine and customary protocols.

Example 15

Pre-Clinical Study

1. Introduction

One important mechanism of arteriogenesis is the induction of shear stress across recruited collateral arteries.

NO plays a fundamental role in this scenario, since it regulates the vasodilatory capability of the artery as well as therapeutic proliferation aspects on the smooth muscle cells of collateral arteries.

Here we evaluated the effects of Nitrolingual Akut® Spray (G. Pohl-Boskamp GmbH & Co. KG, Hohenlockstedt, Germany; U.S. American brand name Nitrolingual® Pumpspray) in a unique non-myocardial infarct arteriogenesis model. Collateral growth in this model is induced via repetitive occlusion of the left anterior descending coronary artery (LAD). Infarct size in these animals was measured as the endpoint at the end of the experiment. Thus, no interference between myocardial infarction and arteriogenesis has weaken the experiment. Moreover we evaluated the effect of acetyl salicylic acid (ASA) in this model of repetitive coronary occlusion as a possible inhibitor of arteriogenesis. We evaluated whether a concomitant application of NO (intermittent use of nitroglycerin) may compensate for this negative effect of ASA.

2. Materials and Methods
1.1. Animal Preparation

Male Sprague-Dawley rats (300 g body weight at study start; n=182) are used for experiments. For surgery (day 0), rats are premedicated (ketamine 50 mg/ml plus xylazine 4 mg/ml intraperitoneal) and intubated. Oral intubation (14-G polyethylene tubing) is done under direct observation of the vocal cords with an otoscope. General anesthesia is introduced and maintained by isoflurane inhalation (1.0% to 2.0%, with 100% oxygen). Body temperature is controlled at 37° C. by an electric heating table. Surgery is performed using aseptic technique. The animal is initially placed on its dorsal side and cutaneous clips are fixed. With a BioAmp differential amplifier coupled to a PowerLab data acquisition system (AD Instruments) ECG parameters (heart rate) are monitored and recorded during surgery. The heart is exposed by left thoracotomy. A mini-pneumatic snare occluder (see the Mini-Pneumatic Snare Occluder section for details) is implanted around the mid to proximal left anterior descending coronary artery (LAD). Confirmation that the occluder is functional, i.e., producing myocardial ischemia, is determined initially by observation of blanching and hypokinesis of the left ventricle (LV) and by observation of the electrocardiogram (ST elevation) during inflation. Rats are randomly divided into 4 therapeutic modules:

Module 1: Sham Operation
Module 2: NO intermittent (nitroglycerin)
Module 3: NO continuous (retard preparation of isosorbide dinitrate)
Module 4: NO intermittent plus ASA After instrumentation and measurements, the chest is closed under positive end-expiratory pressure, and the thoracic cavity is evacuated of air. The occluders are tunneled subcutaneously and exteriorized between the scapulae. These catheters are protected by a stainless steel spring coil connected to a ring that is secured subcutaneously between the scapulae. After the surgery, analgesic (buprenorphine 0.05 mg/kg SC) and antibiotic (enrofloxacin 10 mg/kg SC) are administered. Rats are observed in a recovery cage for 2 hours and then transferred to the animal care facility where they are continuously monitored by technicians. For 3 days after the surgery, buprenorphine (0.5 mg/kg SC) is taken for pain. On the third day after the surgery (day 3), ischemic protocol is started. After 5 resp. 10 days (only in module 1A and 2B) of the experimental protocol (day 8 resp. day 13), the rats are anesthetized, and the chest is opened by mid thoracotomy. In the micro-CT group, the hearts are immediately excised. For the final infarct size detection the LAD will be permanently occluded (final permanent occlusion, FPO) and infarct size will be measured via TTC staining.

1.2. Mini-Pneumatic Snare Occluder for Rat Heart

A mini-pneumatic snare occluder is used consisting of a mini-balloon, sheath tubing, suture, and catheter. The balloon (7 mm long) is made of soft latex membrane and is sufficiently pliable to give negligible physical force on the coronary vessels during balloon deflation. The balloon is mounted within an umbrella sheath (3.2 or 4.8 mm in diameter, 12 mm in length; protects the balloon from fibrous infiltration). Prolene (5-0) is passed around the LAD and attached to the sheath, securing the occluder to the heart, so that myocardial ischemia is produced by balloon inflation. Inflation volume is small (0.2 to 0.25 mL air), but occlusion occurs by 2 physical actions: "crimping" the LAD toward upward/outside and compressing the LAD by the inflated balloon/sheath. The balloon is connected to a catheter (PE-50) that is exteriorized. Balloon inflation and deflation are controlled from outside the rat cage.

1.3. Measurements of ECG Parameters

In all four modules (1-4) we will at the beginning (day 3) and the end (day 8 resp. day 13) of the experimental protocol (RIP) perform the coronary occlusion for 40 seconds (equivalent to an occlusion in the RIP; see page 6) and measure ECG parameters to examine the heart rate and ST elevation.

1.4. Coronary Microvascular Imaging With Micro-CT

In addition we propose to use Micro-CT as a further endpoint to image collaterals. One group of rats (3 rats of each group in each module; total of 36 rats) is prepared for coronary vascular visualization via micro-CT. The coronary circulation is filled with contrast medium (yellow microfil) by modification of the methodology for micro-CT study in the rats. The viscosity of the contrast medium enables filling up to coronary arteriolar level with no or minimal filling of capillaries. The excised heart is immediately cannulated by an aortic cannula, and coronary circulation is perfused retrogradely at 85 mm Hg. A perfusate (25° C. to 27° C. saline with 2% procaine) is used to avoid myocardial metabolic contraction and maximally dilate the coronary vasculature. Polyethylene tubing is inserted into the LV via a left appendage through the mitral valve to unload the LV. Warmed contrast medium (42° C.) is injected at a pressure of 85 mmHg for 3 minutes while perfusion pressure is monitored. The heart is cooled by immersion into cold saline (0° C. to 4° C.) until the (yellow microfil) solidified. Then, the heart is removed and fixed in 4% paraformaldehyde solution (4° C.) overnight. Whole hearts are used for micro-CT imaging of coronary collateral growth. The coronary vasculature is visualized with micro-CT. In brief, the whole heart is scanned in 1° increments around 360° about its apex-to-base longitudinal axis. The spatial resolution selected in the present study has an $18*18*18$ m$^3$ voxel size to focus on the size of collateral vessels and to minimize the signals from smaller vessels. Finally, CT data are reconstructed as 3D images. The main purpose of these images is to establish the presence or absence of arterial-arterial anastomotic connections. Collateral vessels, i.e., arterial-arterial anastomotic connections, are counted by independent observers for the groups.

1.5. Experimental Protocol

The repetitive ischemia protocol (RIP) is introduced by automatised inflation of the occluder using the following protocol: 40 seconds of occlusion every 20 minutes for 2 hours 20 minutes, followed by a period of "rest" (deflation) for 5 hours 40 minutes. This 8-hour set is repeated 3 times a day for 5 resp. 10 days (only in module 1A and 2A). The LAD is occluded automatically by remote inflation or deflation through the catheter. In sham rats (see module 1), the balloon is implanted, but RIP is not applied. Rats under RI protocol are randomly divided into the three modules 2, 3 and 4.

1.6. Infarct Size Detection

Infarct size will be detected by TTC staining after final permanent occlusion. After 5 resp. 10 days (only in module 1A and 2A) of the experimental protocol, the occluder is inflated permanently for 90 minutes. Infarct size will be measured by TTC staining (n=10/group). Therefore rats are anaesthesized and undergo again the ECG recording to confirm the occlusion (ST elevation) and to calculate ECG parameters and the numbers of arrhythmias. In animals without collaterals, coronary occlusion causes deterioration of systemic hemodynamics and arrhythmias, including premature ventricular contractions, ventricular tachycardia, and ventricular fibrillation; in animals with well developed collaterals, no such adverse effects are noted.

The chest is opened by mid thoracotomy. The heart is immediately excised and sectioned from apex to base in 2-mm-thick transverse slices parallel to the atrioventricular groove. Slices are incubated with 0.09 mol/L sodium phosphate buffer containing 1.0% triphenyl tetrazolium chloride (TTC) and 8% dextran for 20 min. at 37° C. Slices are fixed in 10% formaldehyde and then photographed with a digital camera mounted on a stereomicroscope. The infarcted size is quantified using a computerized planmetric program (Adobe Photoshop). The infarcted area is indentified as the TTC-negative tissue and is expressed as a percentage of the area of the left ventricle (LV).

1.7. Details Regarding Testing Compounds

| | |
|---|---|
| ASA | Merck Chemicals |
| NO intermittent (NTG) | nitroglycerin solution; Nitrolingual akut ® Spray, G. Pohl-Boskamp GmbH & Co. KG, Hohenlockstedt, Germany |
| NO continuous (ISDN retard) | isosorbide dinitrate retard pellets; Nitrosorbon ® retard; G. Pohl-Boskamp GmbH & Co. KG, Hohenlockstedt, Germany |
| Carrier compound for NO intermittent (NTG-Placebo) | placebo solution of Nitrolingual akut ® Spray, Pohl-Boskamp GmbH & Co. KG, Hohenlockstedt, Germany |
| NO continuous Carrier Compound (ISDN-Placebo) | neutral pellets of Nitrosorbon ® retard; G. Pohl-Boskamp GmbH & Co. KG, Hohenlockstedt, Germany |
| Control buffer | PBS (phosphate buffered saline) |

1.8. Route, Timepoint and Concentration of Delivery to Animals

All medication (ASA and NTG and ISDN retard) is given upfront to a following occlusion time of the device. The control buffer (PBS) is given in the same way prior to the first two occlusions.

NO Intermittent (NTG)

A new test solution is prepared every morning at eight o'clock. The solution is taken from the vials via syringes.

NO intermittent (NTG) is given twice a day with a time interval of 8 hours.

Due to the chronic instrumentation of the rats and to avoid further stress, NTG is given via buccal application. 50 µl of the daily prepared test solution containing 13.3 µg nitroglycerin (equivalent to a human dose of 0.8 mg) is administered per buccal application in module 1, 2 and 4. The time point of application is directly upfront to balloon inflation at 9 a.m. and 5 p.m., thus with maximal effects on recruited collateral arteries.

This concentration is taken from the above mentioned reaction vials right before administration.

Carrier compound solution is served as a stock solution for the preparation of the test solution.

Carrier Compound for NO Intermittent (NTG-Placebo)

Carrier compound is administered in a way identical to NO intermittent.

NO Continuous (ISDN Retard)

The medication for prolonged NO delivery (retard preparation isosorbide dinitrate=long-acting nitrate ISDN) is delivered as retarded pellets 1× per day.

For the retard preparation ISDN a dosage of 2.6 mg ISDN/rat is chosen. Therefore 13 mg pellets are suspended in 0.5 ml drinking water and are applied via gavage at 9 a.m. every morning (equivalent of a human dose of 2 mg/kg/BW).

NO continuous Carrier Compound (ISDN-Placebo)

Carrier compound is administered in a way identical to NO continuous.

No Intermittent Plus ASA (Acetylsalicylic Acid)

Every morning at 9.30 a.m. 2.22 mg ASA per rat is given dissolved in 0.5 ml drinking water via gavage directly into the stomach.

The ASA concentration of 2.22 mg ASA per rat (6.34 mg/kg) correlates with the human dosage of 100 mg/day.

1.9. Animals and Groups 10 rats per groups (FPO=final permanent occlusion to induce infarcts)

Group d: 3 additional animals are treated with the same medications and ligation scheme like the corresponding groups a, b and c, but without FPO. These 9 animals per module are used for micro CT images.

Module 1: Sham Operation (without the RIP):
A. Control buffer (phosphate buffered saline PBS) with functional FPO for infarct size detection n=20
  1. n=10: "5 DAYS SHAM PBS"
  2. n=10 "10 DAYS SHAM PBS"
B. Carrier compound without NO plus functional FPO for infarct size detection
  n=10: "5 DAYS SHAM NTG-PLACEBO"
C. NTG with functional FPO for infarct size detection
  n=10: "5 DAYS SHAM NTG"
D. A1.) n=3 A2.) n=3 B) n=3 C) n=3 for micro CT images
  n=12
  total: n=52

Module 2: NO Intermittent:
A. intermittent control buffer with functional FPO for infarct size detection
  n=20
  1. n=10: "5 DAYS RIP PBS"
  2. n=10: "10 DAYS RIP PBS"
B. intermittent Carrier compound plus functional FPO for infarct size detection
  n=10: "5 DAYS RIP NTG-PLACEBO"
C. Intermittent NTG with functional FPO for infarct size detection
  n=10: "5 DAYS RIP NTG"
D. A1.) n=3 A2.) n=3 B) n=3 C) n=3 for micro CT images
  n=12
  total: n=52

Module 3: NO Continuous:
A. Continuous Control buffer (drinking water) with functional FPO for infarct size detection (n=10): "5 DAYS RIP DW"
B. Continuous Carrier compound plus functional FPO for infarct size detection
  n=10: "5 DAYS RIP ISDN-PLACEBO"
C. Continuous NO functional FPO for infarct size detection
  n=10: "5 DAYS RIP ISDN"
D. A.) n=3 B.) n=3 C.) n=3 for micro CT images
  n=9
  total: n=(39)

Module 4: NO Intermittent Plus ASA:
A. Intermittent Control buffer plus ASA with functional FPO for infarct size detection
n=10: "5 DAYS RIP PBS+ASA"
B. Intermittent NO Carrier compound plus ASA plus functional FPO for infarct size detection n=10: "5 DAYS RIP NTG-PLACEBO+ASA"
C. Intermittent NTG plus ASA functional FPO for infarct size detection
n=10: "5 DAYS RIP NTG+ASA"
D. A.) n=3 B.) n=3 C.) n=3 for micro CT images
n=9
total: n=39

3. Results 3.1 Final Permanent Occlusion

LAD occlusion allowed a prospective study of the function of collateral vessels. Such vessels can protect myocardial tissue at risk of ischemia after coronary occlusion.

At the end of the RMI protocol we performed the permanent LAD occlusion in one subgroup of all groups and measured ECG parameters to examine ST segment elevation and ventricular arrhythmias. After 90 minutes of permanent occlusion we determined the infarcted area.

3.2 ECG Analysis

Electrocardiographic manifestations of ischemia initiated by LAD occlusion are less pronounced when collateral vessels are present.

3.3. ST Segment Elevation

During LAD occlusion there is an inverse correlation between the magnitude of ST segment elevation and the extent of the collateral supply.

Collateral function is an important determinant of the direction of ST segment response to ischemia during acute coronary occlusion. Reversible ST segment elevation during acute LAD occlusion is related to inadequate collateral arterial function. In patients with reversible ST segment depression, coronary collateral function appears to be better and, as a consequence, shows less ischemia results.

Figure 1:
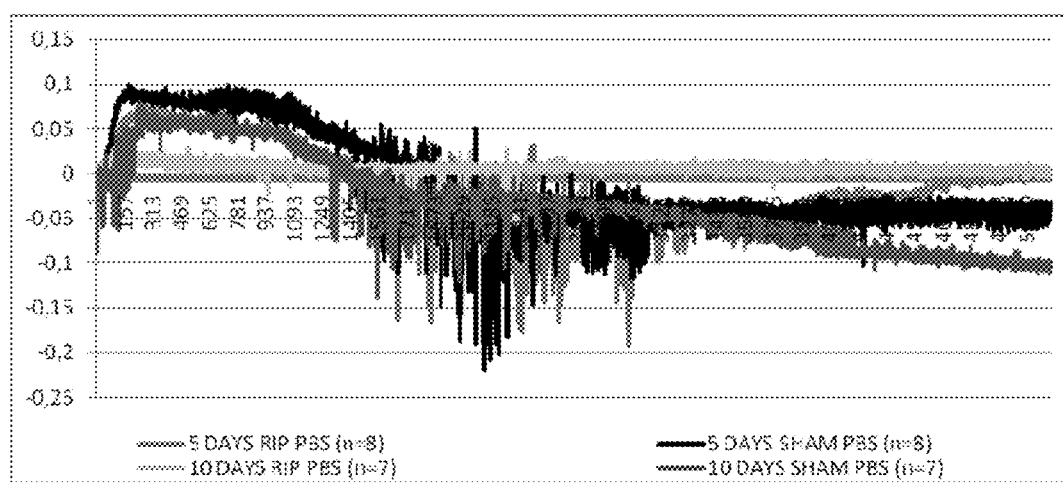
FIG. 1: Course of the ST elevation per beat after FPO of 5- and 10-days control-groups. ECG graph in middle grey indicates 5 DAYS RIP PBS, n=8: 0.104±0.016 mV; ECG graph in black indicates 5 DAYS SHAM PBS, n=8: 0.134±0.034 mV; ECG graph in light grey indicates 10 DAYS RIP PBS, n=7: 0.055±0.033 mV; ECG graph in dark grey indicates 10 DAYS SHAM PBS, n=7: 0.124±0.039 mV.

During a 90 minutes occlusion the ST segment elevation in the "10 DAYS SHAM PBS" is significantly higher compared to the "10 DAYS RIP PBS" group (10 DAYS SHAM, n=7: 0.124±0.039 mV; 10 DAYS RIP, n=7: 0.055±0.033 mV). In contrast, ST segment elevation in the "5 DAYS SHAM PBS" is similar to the "5 DAYS RIP PBS" group (5 DAYS SHAM, n=8: 0.134±0.034 mV; 5 DAYS RIP, n=8: 0.104±0.016 mV) (FIGS. 1 and 2).

Module 1: Sham Operation (without the RIP)

There is no significance between the three SHAM-groups (5 DAYS SHAM PBS, n=8: 0.134±0.034 mV; 5 DAYS SHAM NTG-PLACEBO, n=6: 0.131±0.043 mV; 5 DAYS SHAM NTG, n=7: 0.124±0.058 mV) (FIGS. 3 and 4).

Module 2: NO Intermittent (NTG)

In the NTG group ("5 DAYS RIP NTG") ST elevation is significantly decreased compared to the PBS group (5 DAYS RIP PBS, n=8: 0.104±0.016 mV; 5 DAYS RIP NTG, n=7: 0.052±0.030 mV). There is no significance between the PBS and NTG-PLACEBO-group (5 DAYS NTG-PLACEBO: n=6; 0.096±0.061 mV) (FIGS. 5 and 6).

Module 3: NO Continuous (ISDN Retard)

ST segment elevation in the ISDN group ("5 DAYS RIP ISDN") is decreased compared to the PBS group (5 DAYS RIP PBS, n=8: 0.104±0.016 mV; 5 DAYS RIP ISDN, n=7: 0.062±0.027 mV), but there is no significance as well as between the PBS and ISDN-PLACEBO-group (5 DAYS ISDN-PLACEBO, n=7: 0.110±0.069 mV) (FIGS. 7 and 8).

Module 4: NO Intermittent Plus ASA

ST segment elevation in the group treated with PBS and ASA is higher compared to the PBS control group (5 DAYS RIP ASA+PBS, n=7: 0.138±0.098 mV; 5 DAYS RIP PBS, n=8; 0.104±0.016 mV), but there is no significance as well as between the ASA+NTG-PLACEBO-group (5 DAYS RIP ASA+NTG-PLACEBO, n=6: 0.144±0.091 mV). In the ASA+NTG-group ST elevation is decreased compared to the group treated with ASA and PBS (5 DAYS RIP NTG+ASA, n=7: 0.088±0.071 mV) (FIGS. 9 and 10).

3.4. Ventricular Arrhythmias

The importance of ventricular premature beats (VPBs) results from their possible association with an increased risk for cardiac sudden death. VPBs were stratified according to the Lown classification. A high Lown grade has been shown to predict mortality after acute myocardial infarction.

Grade 0: no ventricular ectopic beats
Grade I: occasional, isolated VPB
Grade II: frequent VPB (>1/min or 30/h)
Grade III: multiform VPB
  (a) VPB
  (b) Bigenimus
Grade IV: repetitive VPB
  (a) Couplets
  (b) Salvos
Grade V: Early VPB Module 1: Sham Operation (without the RIP)

In the "5 DAYS SHAM PBS" group 87.5% of the rats have class IVb arrhythmias and 12.5% class IVa. In the "5 DAYS SHAM NTG-PLACEBO" group 83.3% have IVb arrhythmias and 16.7% class IVa and in the "5 DAYS SHAM NTG" group 85.7% have IVb arrhythmias and 14.3% class IIIa arrhythmias (FIG. 11).

Module 2: NO Intermittent (NTG)

In the "5 DAYS RIP PBS" group, 75.0% of the rats have class IVb arrhythmias, 12.5% IVa and 12.5% class 0. Regarding the "5 DAYS RIP NTG-PLACEBO" group, 66.7% of the rats showed class IVb arrhythmias, 16.7% IVa and 16.7% class IIIb arrhythmias. Interestingly, the "5 DAYS RIP NTG" group shows 42.9% class IVb arrhythmias and 57.1% class 0 arrhythmias (FIG. 12).

Module 3: NO Continuous (ISDN Retard)

In the "5 DAYS ISDN-PLACEBO" group, 57.1% of the rats have class IVb arrhythmias, 14.3% class IVa and 28.6% class IIIb. The "5 DAYS RIP ISDN" group shows less severe arrhythmias with 57.1% class IVb, 28.6% class IVa and 14.3% class 0 arrhythmias (FIG. 13).

Module 4: NO Intermittent Plus ASA

In the "5 DAYS RIP ASA+PBS" group, in the group treated with ASS+NTG-PLACEBO and in the "5 DAYS RIP ASS+NTG" group 83.3% of the rats posses class IVb arrhythmias and 16.7% class IIIa.

Regarding the percentage of each Lown grade of every group, a VBP score can be ascertained. The more animals show a higher grade, the higher is the VBP score (FIG. 15).

FIG. 15: VPB-Score

TABLE 1

| VPB-Score | |
| --- | --- |
| group | VPB-Score |
| Module 1 | |
| SHAM PBS | 5.88 |
| SHAM NTG-PLACEBO | 5.83 |
| SHAM NTG | 5.77 |

TABLE 1-continued

VPB-Score

| group | VPB-Score |
|---|---|
| Module 2 | |
| RIP PBS | 5.10 |
| RIP NTG-PLACEBO | 4.84 |
| RIP NTG | 3.60 |
| Module 3 | |
| RIP PBS | 5.10 |
| RIP ISDN-PLACEBO | 5.29 |
| RIP ISDN | 4.57 |
| Module 4 | |
| RIP ASA + PBS | 5.50 |
| RIP ASA + NTG-PLACEBO | 5.50 |
| RIP ASA + NTG | 5.50 |

3.5. Infarct Size

After 90 minutes of LAD occlusion and 20 minutes reperfusion, infarct size was analyzed. The "10 DAYS RIP PBS" group has a significantly smaller infarct area compared to the "10 DAYS SHAM PBS" group (10 DAYS RIP PBS, n=6: 6.57±3.26%; 10 DAYS SHAM PBS, n=7: 13.71±6.06%). There is no significance between both 5 DAYS groups (5 DAYS SHAM PBS, n=8: 13.36±5.22%; 5 DAYS RIP PBS, n=8: 11.05±5.12%) (FIG. 16).

Module 1: Sham Operation (without the RIP)

There is no significance between the three SHAM-groups (5 DAYS SHAM PBS, n=8: 13.36±5.22 mV; 5 DAYS SHAM NTG-PLACEBO, n=6: 14.21±5.79 mV; 5 DAYS SHAM NTG, n=7: 14.09±5.18 mV) (FIG. 17).

Module 2: NO Intermittent (NTG)

Compared to the "5 DAYS RIP PBS", a significantly smaller infarct area is observed in the "5 DAYS RIP NTG" group (5 DAYS RIP PBS, n=8: 11.05±5.12%; 5 DAYS RIP NTG, n=7: 3.61±2.08%). There is no significance between the PBS and NTG-PLACEBO-group
(5 DAYS NTG-PLACEBO: n=6; 9.80±6.79 mV) (FIG. 18).

Module 3: NO Continuous (ISDN Retard)

The infarct size in the ISDN group ("5 DAYS RIP ISDN") is smaller compared to the PBS group (5 DAYS RIP PBS, n=8: 11.05±5.12%; 5 DAYS RIP ISDN, n=7: 7.59±4.38%), as well as the ISDN-PLACEBO-group (5 DAYS ISDN-PLACEBO, n=6: 9.97±3.65%) (FIG. 19).

Module 4: NO Intermittent Plus ASA

The infarct size in the group treated with ASA ("5 DAYS ASA+PBS") is minimally increased compared to the PBS control group (5 DAYS RIP ASA+PBS, n=6: 12.51±3.05%; 5 DAYS RIP PBS, n=8; 11.05±5.12%), as well as the ASA+NTG-PLACEBO-group (5 DAYS RIP ASA+NTG-PLACEBO, n=6: 13.92±1.71%). There is no difference between the ASA+NTG-group and the group treated with ASA and PBS (FIG. 20). However, the infarct area in the NTG group is significantly smaller compared to the ASA+NTG group (5 DAYS RIP NTG, n=7: 11.05±5.12%; 5 DAYS RIP NTG+ASS, n=6: 13.00±3.82%).

3.6. Coronary Microvascular Imaging with Micro-CT

Collateral arteries are pre-existent vessels running parallel to a major artery. In case the major artery is occluded, even for a short period of time (40 sec during this RIP), collaterals assume the blood supply. As a result, collateral arteries in this area (ROI, region of interest) start to grow in length (clearly visible by the cork screw pattern) and most notably in their diameter. So we measured the diameter of the collaterals in the ROI.

Module 1: Sham Operation (without the RIP)

There is no significance between the three SHAM-groups (5 DAYS SHAM PBS, n=3: 82.7±3.7 μm; 5 DAYS SHAM NTG-PLACEBO, n=3: 89.6 μm±10.6 μm; 5 DAYS SHAM NTG, n=3: 86.8±9.0 μm) (FIGS. 22 and 26).

Module 2: NO Intermittent (NTG)

Compared to the "5 DAYS RIP PBS", the diameters of the collaterals in the ROI in the "5 DAYS RIP NTG" group are significantly increased (5 DAYS RIP PBS, n=3: 129.8±6.9 μm; 5 DAYS RIP NTG, n=3: 158.4±9.2 μm). There is no difference between the PBS and NTG-PLACEBO-group (5 DAYS NTG-PLACEBO: n=3; 127.0±12.1 μm) (FIGS. 23 and 26).

Module 3: NO Continuous (ISDN Retard)

The diameter of the collaterals in the ISDN group ("5 DAYS RIP ISDN") are enhanced compared to the PBS group (5 DAYS RIP PBS, n=3: 129.8±6.9 μm; 5 DAYS RIP ISDN, n=3: 148.2±11.3 μm), as well as compared to the ISDN-PLACEBO group (5 DAYS ISDN-PLACEBO, n=3: 133.0±11.5 μm) (FIGS. 24 and 26).

Module 4: NO Intermittent Plus ASA

The diameter in the group treated with PBS and ASA are smaller compared to the PBS control group (5 DAYS RIP PBS+ASA, n=3: 102.5±8.0 μm; 5 DAYS RIP PBS, n=3; 129.8±6.9 μm), but there is no significance as well as the ASA+NTG-PLACEBO-group (5 DAYS NTG-PLACEBO+ASA, n=3: 97.1±8.61 μm). In the ASA+NTG-group diameter are increased compared to the group treated with PBS and ASA (5 DAYS RIP ASA+NTG, n=3: 124.4±5.6 μm) (FIGS. 25 and 26).

4. Conclusion

We examined the groups "10 DAYS SHAM PBS" and "5 DAYS SHAM PBS", each without a RIP (repetitive ischemic protocol) and the groups "10 DAYS RIP PBS" and "5 DAYS RIP PBS", each with a RIP of five and ten days.

Measurement of infarct volume after a 90 minute permanent LAD occlusion (FPO, final permanent occlusion) revealed significantly smaller infarcted areas in the 10 DAYS RIP group than in "10 DAYS SHAM" group. In contrast, after a RIP of five days, no differences became apparent in the SHAM and RIP group.

Moreover, we used ECG parameters for examinations and evaluation for the first time. We found the maximal ST elevation after FPO of the LAD showed no crucial differences between "5 DAYS RIP PBS" and SHAM groups, yet. However, after 10 days ST elevations were significantly decreased in the RIP group.

Aside from ST elevation measurement during FPO, we were able to analyze and evaluate arrhythmias in differentiated way.

Based on these novel insights into the characterization of rat RMI model, we decided to use a 5 day RIP in case of an expected stimulation of arteriogenesis. The degree of ST elevation enhancement and the infarct volume after a 10 day RIP can be obtained with pro-arteriogenic substances within a 5 day RIP, yet.

This provides additional parameters being able to approve our results of infarct volume measurement.

The intermittent application of NTG solution (twice daily on buccal mucosa) decreased serious arrhythmias of the rat heart during FPO compared to the control group. Additionally, infarct volume is decreased by more than 50% after 90 minutes FPO compared to the control group. This reduction in infarct size is not even obtainable with controls set to a 10 days RIP. Furthermore, a treatment with NTG solution significantly attenuated ST elevation during FPO. On the basis of the μCT analyses, significantly enlarged collateral arteries were measurable.

The treatment of the rats with ISDN retard (once daily intragastrally) also led to decreases in ST elevation during FPO, less arrhythmias and reduced infarct volumes. However, these improvements of infarct parameters are less distinct compared with NTG treatment. Moreover, they did not show any significance.

Compared to controls, the treatment with ASA showed an impairment of ECG parameters and an increase of infarct volumes due to impaired collateral growth. These negative effects of ASA on arteriogenesis are already known. Interestingly, they can be partly abolished through an additional NTG treatment (twice daily on buccal mucosa). Thus, collateral diameters were enlarged in the ROI and ECG parameters were enhanced. Nevertheless, infarct volumes after FPO showed no reduction.

The SHAM groups did not differ among each other.

Further on, there were no differences measured between the Placebo groups and their corresponding control groups.

In conclusion, the presented results indicate that an intermittent treatment with NTG solution decreases the size of an experimentally induced myocardial infarct. In addition, effects on cardiac rhythm may ameliorate. These insights are of outstanding relevance for clinical aspects.

Example 16

Clinical Study

This study aims to investigate the effects of a supervised, physician-controlled standardized exercise program for the symptomatic treatment, functional improvement and an augmentation of the arteriogenic capacity in patients with chronic stable CAD.

1 Study Design
1.1 Hypotheses and Study Arms
1.1.1 Hypotheses
I Active physician-controlled exercise training with intermittent application of GTN is superior to active physician-controlled exercise training without GTN.

(A+)>(A+)

II Passive physician-controlled exercise training (CardioAccel®) with intermittent application of GTN is superior to passive physician-controlled exercise training without GTN.

(P+)>(P-)

III Conservative CAD therapy with intermittent application of GTN is superior to conservative CAD therapy without GTN.

(C+)>(C-)

1.1.2 Study Arms
A+ Active physician-controlled exercise training with intermittent application of GTN
A- Active physician-controlled exercise training
P+ Passive physician-controlled exercise training (CardioAccel) with intermittent application of GTN
P- Passive physician-controlled exercise training (CardioAccel®)
C+ Conservative CAD therapy with intermittent application of GTN
C- Conservative CAD therapy Patients may use GTN in case of angina pectoris, however will be supplied with an additional study GTN for the study use.

Active Physician-Controlled Exercise Training with Intermittent Application of GTN.

Best medical therapy and usual care as detailed in the current guidelines (AHA, ESC) for the care for patients with chronic stable angina. Daily (Mon-Fri) physical exercise intervals (treadmill) of 30 min (≥1 W/kg bw, following risk stratification and individual calculation and adjustment of training intensity as detailed in the current EACPR guidelines, for a total of six weeks. GTN use for the treatment of angina episodes is permitted. In addition, GTN 0.4 mg is administered 2-5 min before the onset of exercise.

Active Physician-Controlled Exercise Training.

Best medical therapy and usual care as detailed in the current guidelines (AHA, ESC) for the care for patients with chronic stable angina. Daily (Mon-Fri) physical exercise intervals (treadmill) of 30 min (≥1 W/kg bw, following risk stratification and individual calculation and adjustment of training intensity as detailed in the current EACPR guidelines, for a total of six weeks. GTN use for the treatment of angina episodes is permitted.

Passive Physician-Controlled Exercise Training (CardioAccel®) with Intermittent Application of GTN.

Best medical therapy and usual care as detailed in the current guidelines (AHA, ESC) for the care for patients with chronic stable angina. Daily (Mon-Fri) CardioAccel® treatment intervals of one hour per day for a total of six weeks, as detailed (Arora R R, Chou T M, Jain D, Fleishman B, Crawford L, McKiernan T, Nesto R W. The multicenter study of enhanced external counterpulsation (MUST-EECP): effect of EECP on exercise-induced myocardial ischemia and anginal episodes. J Am Coll Cardiol. 1999 June; 33(7):1833-40). GTN use for the treatment of angina episodes is permitted. In addition, GTN 0.4 mg is administered 2-5 min before the onset of exercise. GTN use for the treatment of angina episodes is permitted.

Passive Physician-Controlled Exercise Training (CardioAccel®).

Best medical therapy and usual care as detailed in the current guidelines (AHA, ESC) for the care for patients with chronic stable angina. Daily (Mon-Fri) CardioAccel® treatment intervals of one hour per day for a total of six weeks, as detailed (Arora et al., supra). GTN use for the treatment of angina episodes is permitted.

Conservative CAD Therapy with Intermittent Application of GTN.

Best medical therapy and usual care as detailed in the current guidelines (AHA, ESC) for the care for patients with chronic stable angina. GTN use for the treatment of angina episodes is permitted. In addition, GTN 0.4 mg is administered once daily, preferably before the onset of a voluntary activity of daily life.

Conservative CAD Therapy.

Best medical therapy and usual care as detailed in the current guidelines (AHA, ESC) for the care for patients with chronic stable angina. GTN use for the treatment of angina episodes is permitted.

1.2 Clinical Trial Design
1.2.1 Clinical Trial Design—General
The study is designed as a
prospective
randomized
multicenter (German Site, US-Site)
clinical trial, to evaluate glyceryl trinitrate (Nitrolingual) effects on exercise capacity, the proposed pathophysiological mechanism being an induction of pro-arteriogenic effects.

1.2.2 Study Endpoints
Primary
Changes in
functional exercise capacity, as measured on visit 3 by peak volume of oxygen uptake ($VO_2$ max) and maximum oxygen uptake at anaerobic threshold ($VO_2$ max AT) from baseline in a standardized exercise treadmill test (sETT).
Secondary
Changes in
(1) Time to exercise-induced ischemia as measured by time to a >1-mm ST-segment depression in a standardized exercise treadmill test (sETT),
(2) the hemodynamic responses to the sETT, as quantified by the rate-pressure product (RPP)[1], which is defined as the systolic blood pressure (mm Hg) multiplied by the heart rate (bpm). Heart rate, blood pressure, and ST segment trends are electronically measured at the J-point +60 ms,

[1] The Rate-pressure product (RPP) is a sensitive index of myocardial oxygen consumption (mVO2). Patients are categorized by the rate pressure product (RPP) that existed at the time of maximum ST depression. In the absence of ST depression, the Maximum RPP is recorded.

(3) the number of angina episodes per day,
(4) exercise duration on sETT,
(5) Relative Peak Slope Index (RPSI),
(4) Doppler-derived maximal systolic acceleration [ACC-max],
(5) CCS and NYHA functional status,
(6) Duke Treadmill Score[2],

[2] The Duke treadmill score calculates risk; it equals the exercise time in minutes minus (5 times the ST-segment deviation, during or after exercise, in millimeters) minus (4 times the angina index, which has a value of "0" if there is no angina, "1" if angina occurs, and "2" if angina is the reason for stopping the test). Among outpatients with suspected CAD, the two thirds of patients with scores indicating low risk had a four-year survival rate of 99% (average annual mortality rate 0.25%), and the 4% who had scores indicating high risk had a four-year survival rate of 79% (average annual mortality rate 5%). The score works well for both inpatients and outpatients and preliminary data suggest that the score works equally well for men and women [Gibbons et al., 2003 AHA/ACC Guideline]

(7) Incidence of cardiovascular events during the treatment phase and
(8) same as primary endpoint, but one month after intervention period.

1.2.3 Patients
Eligible patients must be clinically stable, receiving before enrolment an antianginal and CAD therapy that is in full accordance with the current ESC/AHA guidelines for the treatment of chronic stable CAD.

Prohibited Medication
    long-acting nitrates
    Sildenafil etc.
    Anti-inflammatory compounds (other than aspirin) such as steroids or etanercept etc.

| Inclusion Criteria: |
| --- |
| Age >18 yrs |
| Documented evidence of stable coronary artery disease by either positive nuclear exercise stress testing, angiographically documented coronary stenosis or history of documented ST-elevation or myocardial infarction |

| Exclusion Criteria: |
| --- |
| Nitrate intolerance or intolerance to any component of the study medication. |
| Medication that poses a risk of pharmacologically interacting with GTN. |
| Acute coronary syndrome or unstable angina ≤6 weeks prior. |
| Left main stenosis of ≥50%. |
| PCI or CABG ≤3 months prior. |

| Exclusion Criteria: |
| --- |
| Coronary angiography ≤3 weeks prior. |
| Congestive heart failure/EF of ≤30%. |
| Valvular heart disease or myocarditis. |
| Uncontrolled hypertension with blood pressure values ≥180/100 mmHg |
| Severe symptomatic PAD, varicosis, deep vein thrombosis (current or in documented medical history), phlebitis or ulcer. |
| Coagulation disorder or therapeutic anticoagulation. |
| Cardiac arrhythmias that interfere with ECP triggering. |
| ECG characteristics that would invalidate ST segment monitoring: baseline ST segment depression, pacemaker-dependent rhythms, QRS duration >0.12 s, arrhythmias other than sinus arrhythmia. |
| FEV1 < 1.5l. |
| Current participation in a cardiac exercise rehabilitation program. |

Randomization
Enrolled patients are randomized in a 1:1:1 ratio to receive/undergo either active training, CardioAccel® therapy or usual care, i.e. a continuation of the baseline treatment in accordance with current guidelines. Within these groups, patients are randomized in a 1:1 ration to either a "+GTN" or a "−GTN" group to receive glycerol trinitrate either in addition to their standard medication, or not.

1.2.4 Study Planning, Conduction and Management
The trial is planned by Arteriogenesis Network Art.Net.
Study management will be covered by Arteriogenesis Network Art.Net.
    c/o Campus Technologies Freiburg GmbH
    Technology Transfer of the University of Freiburg
    CEO: Prof. Dr. Bernhard Arnolds
    Stefan-Meier Straβe 8, 79104 Freiburg (Germany)
    Phone: +49 (0)761 203 4990
    Facsimile: +49 (0)761 203 4992
    Sponsor of the trial is CTF.

The reporting structures and reporting schemes will be detailed after the participating centers have been assigned.
Research Sites
participating centers: to be determined
contact in case of questions, dissemination of info
contact in case of adverse event, dissemination of info 1.2.5 Study Flow Chart and Protocol
The Study Flow Chart is given in FIG. 27.

1.2.6 Treatment Assignment
Randomization will be done at the conducting centers via envelopes.
Stratification will be done according to age-groups, gender and morbidity.
Study visits are conducted by an investigator.
Study centers in advance assign blinded investigators that are unaware of the randomization, and who carry out the medical examinations and testing at Baseline and First Follow-up.
At each study visit, patients are instructed to fill in a short standardized quality of life assessment form (SF-36[3]).

[3] http://www.rand.org/health/surveys_tools/mos/mos_core_36item.html

Patients assigned to the C+/C− groups are contacted on a regular basis by study personnel to help control potential bias effects as these subjects do not have as regular contacts with study personnel as do the CardioAccel® or exercise groups.

1.2.7 Study Visits
Visit 1: Eligibility Screening (Day 1)
    Medical history, including previous interventions, physical exam
    Enrolment y/n Visit 2: Baseline Visit (Until Day 14 (+3 Days))
  Detailed medical history and physical exam, including assessment of number of angina episodes per day, CCS and NYHA status and assessment of voluntary physical activity.
  Treadmill testing on a standard, calibrated treadmill equipment with cardiopulmonary testing capability (modified Naughton protocol): functional exercise capacity ($VO_2$ max and $VO_2$ max AT), time to exercise-induced ischemia as measured by time to a >1-mm ST-segment depression, rate-pressure product (RPP), heart rate, blood pressure, and ST segment trends electronically measured at the J-point+60 ms, exercise duration, DUKE treadmill score,
  continuous monitoring of vital signs incl. 12-lead ECG and $VO_2$, with $VO_2$max defined as $VO_2$ at maximum level of exercise the individual patient is able to achieve (respiratory ratio>1, anaerobic threshold)
  Relative Peak Slope Index (RPSI)
  Doppler-derived maximal systolic acceleration [ACCmax]
  Randomization
Interim Visits (Non-Scheduled)
  Patients are advised to contact the study center at any time regarding their medical condition. Patients are scheduled to return for their first follow-up visits at 6 weeks after randomization.
Visit 3: Short-Term Follow-Up (1-3 Days after Intervention Period)
  Medical history and physical exam, including assessment of number of angina episodes per day, CCS and NYHA status and assessment of voluntary physical activity.
  Treadmill testing on a standard, calibrated treadmill equipment with cardiopulmonary testing capability (modified Naughton protocol):
  functional exercise capacity ($VO_2$ max and $VO_2$ max AT), time to exercise-induced ischemia as measured by time to a >1-mm ST-segment depression, rate-pressure product (RPP), heart rate, blood pressure, and ST segment trends electronically measured at the J-point +60 ms, exercise duration, DUKE treadmill score,
  continuous monitoring of vital signs incl. 12-lead ECG and $VO_2$, with $VO_2$max defined as $VO_2$ at maximum level of exercise the individual patient is able to achieve (respiratory ratio>1, anaerobic threshold)
  Relative Peak Slope Index (RPSI)
  Doppler-derived maximal systolic acceleration [ACCmax]
  Incidence of cardiovascular events during the treatment phase
Visit 4: Long-Term Follow-Up (1 Month after Intervention Period)
(The rational of this study point is to evaluate the long term effect of the study medication after the intervention period).
  Medical history and physical exam, including assessment of number of angina episodes per day, CCS and NYHA status and assessment of voluntary physical activity.
  Treadmill testing on a standard, calibrated treadmill equipment with cardiopulmonary testing capability (modified Naughton protocol):
  functional exercise capacity ($VO_2$ max and $VO_2$ max AT), time to exercise-induced ischemia as measured by time to a >1-mm ST-segment depression, rate-pressure product (RPP), heart rate, blood pressure, and ST segment trends electronically measured at the J-point+60 ms, exercise duration, DUKE treadmill score,
  continuous monitoring of vital signs incl. 12-lead ECG and $VO_2$, with $VO_2$max defined as $VO_2$ at maximum level of exercise the individual patient is able to achieve (respiratory ratio>1, anaerobic threshold)
  Relative Peak Slope Index (RPSI)
  Doppler-derived maximal systolic acceleration [ACCmax]

1.2.8 Statistical Considerations

The main efficacy parameter is functional exercise capacity, as measured by peak volume of oxygen uptake (VO2 max) and maximum oxygen uptake at anaerobic threshold (VO2 max AT) in a standardized exercise treadmill test (sETT). We assume no difference at baseline but significantly higher values in the GTN groups at follow-up.

Statistical Methods

There are two major sources of variance to be considered in this trial: GTN treatment effects and effects of active training/passive training/conservative therapy. Accordingly data will be analysed in a two-way ANOVA. Any therapy effects not related to GTN will be reported in a descriptive way without inference statistic.

For secondary parameters parametric or non-parametric tests will be applied as appropriate.

Sample Size/Power

To establish the necessary sample size for the proposed two-way-ANOVA, we made the following assumptions (based on literature review and internal data): statistical power=80%, standard deviation for outcome measure=15% of mean, effect size (group difference in change between GTN yes/no)=5% of mean. Power was established in a Monte Carlo simulation based on 10000 repeats per sample size over a range of n per group from 30 to 60 patients. This simulation established a minimum sample size of 48 subjects per group, to allow for potential drop-outs we propose to include 50 subjects per group, resulting in a total sample size of 300 patients.

1.3 Ethical and Legal Aspects

The investigators plan and conduct any experiments involving humans, including identifiable samples taken from humans and identifiable data, in compliance with
(a) the Declaration of Helsinki (Ethical Principles for Medical Research Involving Human Subjects) concluded by the World Medical Association (WMA) in June 1964, as last revised;
(b) the ICH Harmonised Tripartite Guideline: Guideline for Good Clinical Practice E6/International Conference on Harmonisation of Technical Requirements for Registration of Pharmaceuticals for Human Use (ICH E6, 1 May 1996) as well as
(c) applicable German regulations (e.g. Arzneimittelgesetz) in their current forms, as well as applicable FDA regulations (e.g. Guidance for Sponsors, Investigators, Informed Consent Elements, 21 CFR §50.25(c).

5. List of Abbreviations $ACC_{max}$: Doppler-derived maximal systolic acceleration
Art.Net.: Network Subcontractors of CTF
CAD: Coronary Artery Disease
CardioAccel®: personalized counterpulsation therapy
CCS: Canadian Class Society (Angina classification)
CTF: Campus Technologies Freiburg
FSS: fluid shear stress
GTN: glyceryl trinitrate
IABP: intra-aortic ballon pump
NYHA: New York Heart Association
RPSI: Relative Peak Slope Index
sETT: a standardized exercise treadmill test
SMC: vascular smooth muscle cell
$VO_2$ max: peak volume of oxygen uptake
$VO_2$ max AT: maximum oxygen uptake at anaerobic threshold

What is claimed is:

1. A method of treating or preventing an arterial insufficiency via induction of arteriogenesis, wherein a NO donor agent is administered in an intermitting manner to a subject in an amount effective for promoting arteriogenesis sufficient to augment collateral circulation, and wherein the NO donor agent is GTN in a solid pharmaceutical preparation for oromucosal, lingual, sublingual, buccal or transmucosal administration characterized in that it contains an absorbate comprising between 0.05 and 2 weight % GTN and a non-volatile ester stabilizer on a carrier material.

2. The method of claim 1, wherein the NO donor agent is administered at least once a day and at least on one day a week for one to two weeks.

3. The method of claim 1, wherein the NO donor agent is administered for a period of weeks selected from the group consisting of: 3 to 6, 3 to 8, 3 to 10, 4 to 8, 4 to 10 and 4 to 12 weeks.

4. The method of claim 1, wherein the NO donor agent is administered in a dosage of between 0.1 and 8 mg per day.

5. The method of claim 1, wherein the NO donor agent is administered in a dosage of between 0.2 and 0.8 mg for 1- up to maximal 4-times daily and not to exceed a maximal daily dosage of 3.2 mg.

6. The method of claim 1, wherein the NO donor agent is administered on 2, 3, 4, 5, 6 or 7 days a week.

7. The method of claim 1, wherein the NO donor agent is administered for 2 or 3 years.

8. The method of claim 1, wherein the NO donor agent is administered for 10 years.

* * * * *